(12) United States Patent
Francischelli et al.

(10) Patent No.: US 7,250,048 B2
(45) Date of Patent: Jul. 31, 2007

(54) ABLATION SYSTEM AND METHOD OF USE

(75) Inventors: David E. Francischelli, Anoka, MN (US); Scott E. Jahns, Hudson, WI (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 10/923,178

(22) Filed: Aug. 20, 2004

(65) Prior Publication Data
US 2005/0090815 A1      Apr. 28, 2005

Related U.S. Application Data

(63) Continuation-in-part of application No. 10/364,553, filed on Feb. 11, 2003, now Pat. No. 6,989,010, which is a continuation-in-part of application No. 10/132,379, filed on Apr. 24, 2002, now Pat. No. 6,648,883.

(60) Provisional application No. 60/287,202, filed on Apr. 26, 2001.

(51) Int. Cl.
*A61B 18/18* (2006.01)
(52) U.S. Cl. ........................ 606/32; 128/898; 606/41; 606/51
(58) Field of Classification Search ............ 606/10–52; 128/898
See application file for complete search history.

(56) References Cited

U.S. PATENT DOCUMENTS

| 3,736,936 A | 6/1973 | Basiulis et al. |
| 3,807,403 A | 4/1974 | Stumpf et al. |
| 3,823,575 A | 7/1974 | Parel |

(Continued)

FOREIGN PATENT DOCUMENTS

WO      WO 94/24949      11/1994

(Continued)

OTHER PUBLICATIONS

Chitwood, "Will C. Sealy, MD: The Father of Arrhythmia Surgery—The Story of the Fisherman with a Fast Pulse," Annals of Thoracic Surgery 58:1228-1239, 1994.

(Continued)

*Primary Examiner*—Henry M Johnson, III
(74) *Attorney, Agent, or Firm*—Mike Jaro; Jeffrey J. Hohenshell

(57) ABSTRACT

A system and method for creating lesions and assessing their completeness or transmurality. Assessment of transmurality of a lesion is accomplished by monitoring the impedance of the tissue to be ablated. Rather than attempting to detect a desired drop or a desired increase impedance, completeness of a lesion is detected in response to the measured impedance remaining at a stable level for a desired period of time, referred to as an impedance plateau. The mechanism for determining transmurality of lesions adjacent individual electrodes or pairs may be used to deactivate individual electrodes or electrode pairs, when the lesions in tissue adjacent these individual electrodes or electrode pairs are complete, to create an essentially uniform lesion along the line of electrodes or electrode pairs, regardless of differences in tissue thickness adjacent the individual electrodes or electrode pairs. Complete or partial submersion in a fluid of the ablating portion of the ablation device may be detected prior to, during or following an ablation procedure.

18 Claims, 12 Drawing Sheets

U.S. PATENT DOCUMENTS

| | | |
|---|---|---|
| 3,823,718 A | 7/1974 | Tromovitch |
| 3,827,436 A | 8/1974 | Stumpf et al. |
| 3,830,239 A | 8/1974 | Stumpf |
| 3,859,986 A | 1/1975 | Okada et al. |
| 3,862,627 A | 1/1975 | Hans, Sr. |
| 3,886,945 A | 6/1975 | Stumpf et al. |
| 3,907,339 A | 9/1975 | Stumpf et al. |
| 3,910,277 A | 10/1975 | Zimmer |
| 3,913,581 A | 10/1975 | Ritson et al. |
| 3,924,628 A | 12/1975 | Droegemueller et al. |
| 4,018,227 A | 4/1977 | Wallach |
| 4,022,215 A | 5/1977 | Benson |
| 4,061,135 A | 12/1977 | Widran et al. |
| 4,063,560 A | 12/1977 | Thomas et al. |
| 4,072,152 A | 2/1978 | Linehan |
| 4,082,096 A | 4/1978 | Benson |
| 4,207,897 A | 6/1980 | Lloyd et al. |
| 4,248,224 A | 2/1981 | Jones |
| 4,275,734 A | 6/1981 | Mitchiner |
| 4,278,090 A | 7/1981 | van Gerven |
| 4,377,168 A | 3/1983 | Rzasa et al. |
| 4,519,389 A | 5/1985 | Gudkin et al. |
| 4,598,698 A | 7/1986 | Siegmund |
| 4,601,290 A | 7/1986 | Effron et al. |
| 4,664,110 A | 5/1987 | Schanzlin |
| 4,736,749 A | 4/1988 | Lundback |
| 4,779,611 A | 10/1988 | Grooters et al. |
| 4,802,475 A | 2/1989 | Weshahy |
| 4,815,470 A | 3/1989 | Curtis et al. |
| 4,872,346 A | 10/1989 | Kelly-Fry et al. |
| 4,916,922 A | 4/1990 | Mullens |
| 4,917,095 A | 4/1990 | Fry et al. |
| 4,936,281 A | 6/1990 | Stasz |
| 4,946,460 A | 8/1990 | Merry et al. |
| 5,013,312 A | 5/1991 | Parins et al. |
| 5,029,574 A | 7/1991 | Shimamura et al. |
| 5,044,165 A | 9/1991 | Linner et al. |
| 5,078,713 A | 1/1992 | Varney |
| 5,080,102 A | 1/1992 | Dory |
| 5,080,660 A | 1/1992 | Buelna |
| 5,100,388 A | 3/1992 | Behl et al. |
| 5,108,390 A | 4/1992 | Potocky et al. |
| 5,147,355 A | 9/1992 | Friedman et al. |
| 5,178,133 A | 1/1993 | Pena |
| 5,207,674 A | 5/1993 | Hamilton |
| 5,217,860 A | 6/1993 | Fahy et al. |
| 5,222,501 A | 6/1993 | Ideker et al. |
| 5,224,943 A | 7/1993 | Goddard |
| 5,228,923 A | 7/1993 | Hed |
| 5,231,995 A | 8/1993 | Desai |
| 5,232,516 A | 8/1993 | Hed |
| 5,233,515 A | 8/1993 | Cosman ............. 364/413.02 |
| 5,254,116 A | 10/1993 | Baust et al. |
| 5,263,493 A | 11/1993 | Avitall |
| 5,269,291 A | 12/1993 | Carter |
| 5,275,595 A | 1/1994 | Dobak, III |
| 5,277,201 A | 1/1994 | Stern |
| 5,281,213 A | 1/1994 | Milder et al. |
| 5,281,215 A | 1/1994 | Milder |
| 5,295,484 A | 3/1994 | Marcus et al. |
| 5,300,068 A | 4/1994 | Rosar et al. ............. 606/34 |
| 5,309,896 A | 5/1994 | Moll et al. |
| 5,316,000 A | 5/1994 | Chapelon et al. |
| 5,317,878 A | 6/1994 | Bradshaw et al. |
| 5,318,525 A | 6/1994 | West et al. |
| 5,322,520 A | 6/1994 | Milder |
| 5,323,781 A | 6/1994 | Ideker et al. |
| 5,324,255 A | 6/1994 | Passafaro et al. |
| 5,324,284 A | 6/1994 | Imran |
| 5,324,286 A | 6/1994 | Fowle |
| 5,334,181 A | 8/1994 | Rubinsky et al. |
| 5,334,193 A | 8/1994 | Nardella ................. 606/41 |
| 5,341,807 A * | 8/1994 | Nardella ................. 600/381 |
| 5,342,357 A | 8/1994 | Nardella ................. 606/40 |
| 5,348,554 A | 9/1994 | Imran et al. |
| 5,353,783 A | 10/1994 | Nakao et al. |
| 5,354,258 A | 10/1994 | Dory |
| 5,361,752 A | 11/1994 | Moll et al. |
| 5,385,148 A | 1/1995 | Lesh et al. |
| 5,396,887 A | 3/1995 | Imran |
| 5,397,304 A | 3/1995 | Truckai |
| 5,400,770 A | 3/1995 | Nakao et al. |
| 5,400,783 A | 3/1995 | Pomeranz et al. |
| 5,403,309 A | 4/1995 | Coleman et al. |
| 5,403,311 A | 4/1995 | Abele et al. ............. 606/49 |
| 5,405,376 A | 4/1995 | Mulier et al. |
| 5,409,483 A | 4/1995 | Campbell et al. |
| 5,423,807 A | 6/1995 | Milder |
| 5,423,811 A | 6/1995 | Imran et al. |
| 5,427,119 A | 6/1995 | Swartz et al. |
| 5,431,649 A | 7/1995 | Mulier et al. ............. 606/41 |
| 5,433,708 A | 7/1995 | Nichols et al. |
| 5,435,308 A | 7/1995 | Gallup et al. |
| 5,437,651 A | 8/1995 | Todd et al. |
| 5,437,664 A | 8/1995 | Cohen et al. ............. 606/42 |
| 5,443,463 A | 8/1995 | Stern et al. |
| 5,443,470 A | 8/1995 | Stern et al. |
| 5,450,843 A | 9/1995 | Moll et al. |
| 5,452,582 A | 9/1995 | Longsworth |
| 5,452,733 A | 9/1995 | Sterman et al. |
| 5,456,662 A | 10/1995 | Edwards et al. ............. 606/31 |
| 5,462,545 A | 10/1995 | Wang et al. |
| 5,465,717 A | 11/1995 | Imran et al. |
| 5,469,853 A | 11/1995 | Law et al. |
| 5,472,876 A | 12/1995 | Fahy |
| 5,478,309 A | 12/1995 | Sweezer et al. |
| 5,478,330 A | 12/1995 | Imran et al. |
| 5,486,193 A | 1/1996 | Bourne et al. |
| 5,487,385 A | 1/1996 | Avitall |
| 5,487,757 A | 1/1996 | Truckai et al. |
| 5,496,312 A | 3/1996 | Klicek |
| 5,497,774 A | 3/1996 | Swartz et al. |
| 5,498,248 A | 3/1996 | Milder |
| 5,500,012 A | 3/1996 | Brucker et al. |
| 5,505,730 A | 4/1996 | Edwards |
| 5,516,505 A | 5/1996 | McDow |
| 5,520,682 A | 5/1996 | Baust et al. |
| 5,522,870 A | 6/1996 | Ben-Zion |
| 5,536,267 A | 7/1996 | Edwards et al. |
| 5,540,681 A | 7/1996 | Strul et al. ............. 606/34 |
| 5,540,684 A | 7/1996 | Hassler, Jr. ............. 606/40 |
| 5,542,928 A | 8/1996 | Evans et al. ............. 604/113 |
| 5,545,195 A | 8/1996 | Lennox et al. |
| 5,545,200 A | 8/1996 | West et al. |
| 5,549,661 A | 8/1996 | Kordis et al. |
| 5,555,883 A | 9/1996 | Avitall |
| 5,558,671 A | 9/1996 | Yates ............. 606/38 |
| 5,560,362 A | 10/1996 | Sliwa, Jr. et al. |
| 5,562,720 A | 10/1996 | Stern et al. |
| 5,562,721 A | 10/1996 | Marchlinski et al. ......... 607/99 |
| 5,569,241 A | 10/1996 | Edwards |
| 5,571,088 A | 11/1996 | Lennox et al. |
| 5,571,215 A | 11/1996 | Sterman et al. |
| 5,573,532 A | 11/1996 | Chang et al. |
| 5,575,766 A | 11/1996 | Swartz et al. |
| 5,575,788 A | 11/1996 | Baker et al. |
| 5,575,810 A | 11/1996 | Swanson et al. |
| 5,578,007 A | 11/1996 | Imran |
| 5,582,609 A | 12/1996 | Swanson et al. |
| 5,584,872 A | 12/1996 | LaFontaine et al. ......... 607/116 |
| 5,588,432 A | 12/1996 | Crowley |
| 5,590,657 A | 1/1997 | Cain et al. |
| 5,595,183 A | 1/1997 | Swanson et al. |
| 5,607,462 A | 3/1997 | Imran |

| Patent No. | Date | Inventor(s) | Class |
|---|---|---|---|
| 5,609,151 A | 3/1997 | Mulier et al. | 128/642 |
| 5,617,854 A | 4/1997 | Munsif | |
| 5,630,837 A | 5/1997 | Crowley | |
| 5,637,090 A | 6/1997 | McGee et al. | |
| 5,643,197 A | 7/1997 | Brucker et al. | |
| 5,653,692 A | 8/1997 | Masterson et al. | 604/113 |
| 5,656,029 A | 8/1997 | Imran et al. | |
| 5,658,278 A | 8/1997 | Imran et al. | |
| 5,671,747 A | 9/1997 | Connor | |
| 5,673,695 A | 10/1997 | McGee et al. | |
| 5,673,704 A | 10/1997 | Marchlinski et al. | 128/739 |
| 5,676,662 A | 10/1997 | Fleischhacker et al. | |
| 5,676,692 A | 10/1997 | Sanghvi et al. | |
| 5,676,693 A | 10/1997 | LaFontaine | 607/116 |
| 5,678,550 A | 10/1997 | Bassen et al. | |
| 5,680,860 A | 10/1997 | Imran | |
| 5,681,278 A | 10/1997 | Igo et al. | |
| 5,681,308 A | 10/1997 | Edwards et al. | |
| 5,687,723 A | 11/1997 | Avitall | |
| 5,687,737 A | 11/1997 | Branham et al. | |
| 5,688,267 A | 11/1997 | Panescu et al. | |
| 5,690,611 A | 11/1997 | Swartz et al. | 604/53 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | |
| 5,697,909 A | 12/1997 | Eggers et al. | 604/114 |
| 5,697,925 A | 12/1997 | Taylor | |
| 5,697,927 A | 12/1997 | Imran et al. | 606/41 |
| 5,697,928 A | 12/1997 | Walcott et al. | |
| 5,713,896 A | 2/1998 | Nardella | 606/50 |
| 5,713,942 A | 2/1998 | Stern | |
| 5,716,389 A | 2/1998 | Walinsky et al. | |
| 5,718,241 A | 2/1998 | Ben-Haim et al. | |
| 5,718,701 A | 2/1998 | Shai et al. | |
| 5,720,775 A | 2/1998 | Larnard | |
| 5,722,402 A | 3/1998 | Swanson et al. | |
| 5,722,975 A * | 3/1998 | Edwards et al. | 606/34 |
| 5,725,524 A | 3/1998 | Mulier et al. | 606/41 |
| 5,730,074 A | 3/1998 | Peter | |
| 5,730,127 A | 3/1998 | Avitall | |
| 5,730,704 A | 3/1998 | Avitall | |
| 5,733,280 A | 3/1998 | Avitall | 606/23 |
| 5,733,281 A | 3/1998 | Nardella | 606/38 |
| 5,735,280 A | 4/1998 | Sherman et al. | |
| 5,735,290 A | 4/1998 | Sterman et al. | |
| 5,749,869 A | 5/1998 | Lindenmeier et al. | 606/34 |
| 5,755,760 A | 5/1998 | Maguire et al. | |
| 5,769,846 A | 6/1998 | Edwards et al. | |
| 5,782,828 A | 7/1998 | Chen et al. | |
| 5,785,706 A | 7/1998 | Bednarek | |
| 5,788,636 A | 8/1998 | Curley | |
| 5,792,140 A | 8/1998 | Tu et al. | |
| 5,797,960 A | 8/1998 | Stevens et al. | |
| 5,800,428 A | 9/1998 | Nelson et al. | |
| 5,800,482 A | 9/1998 | Pomeranz et al. | 607/101 |
| 5,807,395 A * | 9/1998 | Mulier et al. | 606/41 |
| 5,810,802 A | 9/1998 | Panescu et al. | |
| 5,827,216 A | 10/1998 | Igo et al. | |
| 5,836,874 A * | 11/1998 | Swanson et al. | 600/374 |
| 5,836,947 A | 11/1998 | Fleischman et al. | |
| 5,840,030 A | 11/1998 | Ferek-Petric et al. | |
| 5,844,349 A | 12/1998 | Oakley et al. | |
| 5,846,187 A | 12/1998 | Wells et al. | |
| 5,846,191 A | 12/1998 | Wells et al. | |
| 5,849,028 A | 12/1998 | Chen | |
| 5,868,739 A | 2/1999 | Lindenmeier et al. | 606/39 |
| 5,871,523 A | 2/1999 | Fleischman et al. | |
| 5,871,525 A | 2/1999 | Edwards et al. | |
| 5,873,845 A | 2/1999 | Cline et al. | |
| 5,876,398 A | 3/1999 | Mulier et al. | 606/41 |
| 5,876,399 A | 3/1999 | Chia et al. | |
| 5,879,295 A | 3/1999 | Li et al. | |
| 5,879,296 A | 3/1999 | Ockuly et al. | |
| 5,881,732 A | 3/1999 | Sung et al. | |
| 5,882,346 A | 3/1999 | Pomeranz et al. | |
| 5,885,278 A | 3/1999 | Fleischman | |
| 5,888,198 A | 3/1999 | Eggers et al. | 604/114 |
| 5,891,095 A | 4/1999 | Eggers et al. | 604/114 |
| 5,893,848 A * | 4/1999 | Negus et al. | 606/41 |
| 5,895,417 A | 4/1999 | Pomeranz et al. | 607/101 |
| 5,897,533 A | 4/1999 | Glickman | 606/256 |
| 5,897,552 A | 4/1999 | Edwards et al. | 606/31 |
| 5,897,553 A | 4/1999 | Mulier et al. | 606/41 |
| 5,897,554 A | 4/1999 | Chia et al. | |
| 5,899,898 A | 5/1999 | Arless et al. | |
| 5,899,899 A | 5/1999 | Arless et al. | |
| 5,902,289 A | 5/1999 | Swartz et al. | |
| 5,902,328 A | 5/1999 | LaFontaine et al. | 607/116 |
| 5,904,711 A | 5/1999 | Flom et al. | |
| 5,906,580 A | 5/1999 | Kline-Schoder et al. | |
| 5,906,587 A | 5/1999 | Zimmon | |
| 5,906,606 A | 5/1999 | Chee et al. | |
| 5,906,613 A | 5/1999 | Mulier et al. | 606/41 |
| 5,908,029 A | 6/1999 | Knudson et al. | |
| 5,913,854 A | 6/1999 | Maguire et al. | 606/41 |
| 5,913,856 A | 6/1999 | Chia et al. | 606/41 |
| 5,916,213 A | 6/1999 | Haissaguerre et al. | 606/41 |
| 5,916,214 A | 6/1999 | Cosio et al. | |
| 5,921,924 A | 7/1999 | Avitall | |
| 5,921,982 A | 7/1999 | Lesh et al. | |
| 5,927,284 A | 7/1999 | Borst et al. | |
| 5,928,191 A | 7/1999 | Houser et al. | |
| 5,931,810 A | 8/1999 | Grabek | |
| 5,931,835 A | 8/1999 | Mackey | |
| 5,931,848 A | 8/1999 | Saadat | |
| 5,954,661 A | 9/1999 | Greenspon et al. | |
| 5,957,961 A | 9/1999 | Maguire et al. | 607/99 |
| 5,971,980 A | 10/1999 | Sherman | 606/34 |
| 5,971,983 A | 10/1999 | Lesh | |
| 5,976,128 A | 11/1999 | Schilling et al. | 606/34 |
| 5,993,447 A | 11/1999 | Blewett et al. | |
| 6,007,499 A | 12/1999 | Martin et al. | |
| 6,012,457 A | 1/2000 | Lesh | |
| 6,016,811 A | 1/2000 | Knopp et al. | |
| 6,042,556 A | 3/2000 | Beach et al. | |
| 6,063,081 A | 5/2000 | Mulier | |
| 6,071,279 A | 6/2000 | Whayne et al. | |
| 6,080,149 A | 6/2000 | Huang et al. | 606/32 |
| 6,088,894 A | 7/2000 | Oakley | |
| 6,096,037 A | 8/2000 | Mulier et al. | 606/49 |
| 6,112,123 A | 8/2000 | Kelleher et al. | 607/98 |
| 6,113,592 A | 9/2000 | Taylor | |
| 6,117,101 A | 9/2000 | Diederich et al. | |
| 6,120,496 A | 9/2000 | Whayne et al. | |
| 6,142,992 A * | 11/2000 | Cheng et al. | 606/34 |
| 6,142,993 A | 11/2000 | Whayne et al. | |
| 6,142,994 A | 11/2000 | Swanson et al. | |
| 6,152,920 A | 11/2000 | Thompson et al. | |
| 6,161,543 A | 12/2000 | Cox et al. | |
| 6,162,216 A | 12/2000 | Guziak et al. | |
| 6,165,174 A | 12/2000 | Jacobs et al. | |
| 6,179,834 B1 | 1/2001 | Buysse et al. | 606/41 |
| 6,183,468 B1 | 2/2001 | Swanson et al. | 606/40 |
| 6,217,528 B1 | 4/2001 | Koblish et al. | |
| 6,217,576 B1 | 4/2001 | Tu et al. | |
| 6,224,592 B1 | 5/2001 | Eggers et al. | |
| 6,231,518 B1 | 5/2001 | Grabek et al. | |
| 6,235,020 B1 * | 5/2001 | Cheng et al. | 606/34 |
| 6,235,024 B1 | 5/2001 | Tu | |
| 6,237,605 B1 | 5/2001 | Vaska et al. | |
| 6,238,347 B1 | 5/2001 | Nix et al. | |
| 6,238,393 B1 | 5/2001 | Mulier et al. | |
| 6,245,061 B1 | 6/2001 | Panescu et al. | |
| 6,245,064 B1 | 6/2001 | Lesh et al. | |
| 6,245,065 B1 | 6/2001 | Panescu et al. | |
| 6,251,092 B1 | 6/2001 | Qin et al. | |

| | | |
|---|---|---|
| 6,251,128 B1 | 6/2001 | Knopp et al. |
| 6,270,471 B1 | 8/2001 | Hechel et al. |
| 6,293,943 B1 | 9/2001 | Panescu et al. |
| 6,296,619 B1 | 10/2001 | Brisken et al. |
| 6,296,636 B1 * | 10/2001 | Cheng et al. ............... 606/32 |
| 6,302,880 B1 | 10/2001 | Schaer |
| 6,311,692 B1 | 11/2001 | Vaska et al. |
| 6,312,383 B1 | 11/2001 | Lizzi et al. |
| 6,314,962 B1 | 11/2001 | Vaska et al. |
| 6,314,963 B1 | 11/2001 | Vaska et al. |
| 6,325,797 B1 | 12/2001 | Stewart et al. |
| 6,328,736 B1 | 12/2001 | Mulier |
| 6,332,881 B1 | 12/2001 | Carner et al. |
| 6,358,248 B1 | 3/2002 | Mulier |
| 6,361,531 B1 | 3/2002 | Hissong |
| 6,364,876 B1 | 4/2002 | Erb et al. |
| 6,368,275 B1 | 4/2002 | Sliwa et al. |
| 6,371,955 B1 | 4/2002 | Fuimaono et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey et al. ............... 606/34 |
| 6,413,254 B1 | 7/2002 | Hissong et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,447,507 B1 | 9/2002 | Bednarek et al. |
| 6,461,314 B1 | 10/2002 | Pant et al. |
| 6,461,356 B1 | 10/2002 | Patterson |
| 6,464,700 B1 | 10/2002 | Koblish et al. |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,484,727 B1 | 11/2002 | Vaska et al. |
| 6,488,680 B1 | 12/2002 | Francischelli |
| 6,502,575 B1 | 1/2003 | Jacobs et al. |
| 6,514,250 B1 | 2/2003 | Jahns |
| 6,527,767 B2 | 3/2003 | Wang et al. |
| 6,537,248 B2 | 3/2003 | Mulier |
| 6,537,272 B2 | 3/2003 | Christopherson et al. |
| 6,558,382 B2 | 5/2003 | Jahns |
| 6,584,360 B2 | 6/2003 | Francischelli |
| 6,585,732 B2 | 7/2003 | Mulier |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,645,199 B1 | 11/2003 | Jenkins et al. |
| 6,648,883 B2 | 11/2003 | Francischelli |
| 6,656,175 B2 | 12/2003 | Francischelli |
| 6,663,627 B2 | 12/2003 | Francischelli |
| 6,692,450 B1 | 2/2004 | Coleman |
| 6,699,240 B2 | 3/2004 | Francischelli |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,807,968 B2 | 10/2004 | Francischelli |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,960,205 B2 | 11/2005 | Jahns |
| 6,962,589 B2 | 11/2005 | Mulier |
| 2001/0039419 A1 | 11/2001 | Francischelli et al. |
| 2002/0026186 A1 * | 2/2002 | Woloszko et al. ............ 606/41 |
| 2002/0029036 A1 * | 3/2002 | Goble et al. ............... 606/38 |
| 2003/0014047 A1 | 1/2003 | Woloszko et al. |
| 2003/0045872 A1 | 3/2003 | Jacobs |
| 2003/0144656 A1 | 7/2003 | Ocel |
| 2003/0191462 A1 | 10/2003 | Jacobs |
| 2003/0208193 A1 | 11/2003 | Van Wyk |
| 2003/0216724 A1 | 11/2003 | Jahns |
| 2004/0015106 A1 | 1/2004 | Coleman |
| 2004/0015219 A1 | 1/2004 | Francischelli |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0138621 A1 | 7/2004 | Jahns |
| 2004/0138656 A1 | 7/2004 | Francischelli |
| 2004/0143260 A1 | 7/2004 | Francischelli |
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0090815 A1 | 4/2005 | Francischelli |
| 2005/0143729 A1 | 6/2005 | Francischelli |
| 2005/0165392 A1 | 7/2005 | Francischelli |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Christian |

FOREIGN PATENT DOCUMENTS

| | | |
|---|---|---|
| WO | WO 01/87172 | 11/2001 |

OTHER PUBLICATIONS

Gallagher et al., "Cryosurgical Ablation of Accessory Atrioventrical Connections: A Method for Correction of the Pre-excitation Syndrome," Circulation 55(3): 471-479, 1977.

Sealy, "Direct Surgical Treatment of Arrhythmias: The Last Frontier in Surgical Cardiology," Chest 75(5): 536-537, 1979.

Sealy, "The Evolution of the Surgical Methods for Interruption of Right Free Wall Kent Bundles," The Annals of Thoracic Surgery 36(1): 29-36, 1983.

Guiraudon et al., "Surgical Repair of Wolff-Parkinson-White Syndrome: A New Closed-Heart Technique," The Annals of Thoracic Surgery 37(1): 67-71, 1984.

Klein et al., "Surgical Correction of the Wolff-Parkinson-White Syndrome in the Closed Heart Using Cryosurgery: A Simplified Approach," JACC 3(2): 405-409, 1984.

Randall et al., "Local Epicardial Chemical Ablation of Vagal Input to Sino-Atrial and Atrioventricular Regions of the Canine Heart," Journal of the Autonomic Nervous System 11:145-159, 1984.

Guiraudon et al., "Surgical Ablation of Posterior Septal Accessory Pathways in the Wolf-Parkinson-White Syndrome by a Closed Heart Technique," Journal Thoracic Cardiovascular Surgery 92:206-413, 1986.

Gallagher et al., "Surgical Treatment of Arrhythmias," The American Journal of Cardiology 61:27A-44A, 1988.

Mahomed et al., "Surgical Division of Wolff-Parkinson-White Pathways Utilizing the Closed-Heart Technique: A 2-Year Experience in 47 Patients," The Annals of Thoracic Surgery 45(5): 495-504, 1988.

Cox et al., Surgery for Atrial Fibrillation; Seminars in Thoracic and Cardiovascular Surgery, vol. 1, No. 1 (Jul. 1989) pp. 67-73.

Bredikis and Bredikis; Surgery of Tachyarrhythmia: Intracardiac Closed Heart Cryoablation; PACE, vol. 13, pp. 1980-1984.

McCarthy et al., "Combined Treatment of Mitral Regurgitation and Atrial Fibrillation with Valvuloplasty and the Maze Procedure," The American Journal of Cardiology 71: 483-486, 1993.

Yamauchi et al. "Use of Intraoperative Mapping to Optimize Surgical Ablation of Atrial Flutter," The Annals of Thoracic Surgery 56: 337-342, 1993.

Graffigna et al., "Surgical Treatment of Wolff-Parkinson-White Syndrome: Epicardial Approach Without the Use of Cardiopulmonary Bypass," Journal of Cardiac Surgery 8: 108-116, 1993.

Siefert et al., "Radiofrequency Maze Ablation for Atrial Fibrillation," Circulation 90(4): I-594. Surgical treatment of atrial fibrillation: a review; Europace (2004) 5, S20-S29.

Elvan et al., "Radiofrequency Catheter Ablation of the Atria Reduces Inducibility and Duration of Atrial Fibrillation in Dog," Circulation 91: 2235-2244, 1995.

Cox et al., "Modification of the Maze Procedure for Atrial Flutter and Atrial Fibrillation. I. Rational and Surgical Results," The Journal of Thoracic Cardiovascular Surgery 110: 473-484, 1995.

Cox, "The Maze III Procedure for Treatment of Atrial Fibrillation," Sabiston DC, ed Atlas of Cardiothoracic Surgery, Philadelphiia: WB Saunders: 460-475, 1994.

Sueda et al., "Simple Left Atrial Procedure for Chronic Atrial Fibrillation Associated with Mitral Valve Disease," The Annals of Thoracic Surgery 62(6): 1796-1800, 1996.

Tsui et al., "Maze 3 for Atrial Fibrillation: Two Cuts Too Few?" PACE 17: 2163-2166, 1994.

Kosakai et al., "Cox Maze Procedure for Chronic Atrial Fibrillation Associated with Mitral Valve Disease," The Journal of Thoracic Cardiovascular Surgery 108: 1049-1055, 1994.

Cox et al., "The Surgical Treatment of Atrial Fibrillation, IV Surgical Technique," J of Thorac Cardiovasc Surg, 1991: 101: 584-593.

Nardella, "Radio Frequency Energy and Impedance Feedback," SPIE vol. 1068, Catheter Based Sensing and Imaging Technology (1989).

Avitall et. al., "A Thoracoscopic Approach to Ablate Atrial Fibrillation Via Linear Radiofrequency Lesion Generation on the Epicardium of Both Atria," PACE, Apr. 1996;19(Part II):626,#241.

Sie et al., "Radiofrequency Ablation of Atrial Fibrillation in Patients Undergoing Mitral Valve Surgery. First Experience," Circulation (Nov. 1996) 96:250,I-675,#3946.

Sie et al., "Radiofrequency Ablation of Atrial Fibrillation in Patients Undergoing Valve Surgery," Circulation (Nov. 1997) 84:I450,#2519.

Jais et al., "Catheter Ablation for Paroxysmal Atrial Fibrillation: High Success Rates with Ablation in the Left Atrium," Circulation (Nov. 1996) 94.I-675,#3946.

Cox, "Evolving Applications of the Maze Procedure for Atrial Fibrillation," Ann Thorac Surg, 1993;55:578-580.

Cox et al. "Five-Year Experience with the Maze Procedure for Atrial Fibrillation," Ann Thorac Surg, 1993; 56:814-824.

Avitall et al., "New Monitoring Criteria for Transmural Ablation of Atrial Tissues," Circulation, 1996;94(Supp 1):I-493, #2889.

Cox et al., "An 8 1/2 Year Clinical Experience with Surgery for Atrial Fibrillation," Annals of Surgery, 1996;224(3):267-275.

Haissaguerre et al., "Radiofrequency Catheter Ablation for Paroxysmal Atrial Fibrillation in Humans: Elaboration of a procedure based on electrophysiological data," Nonpharmacological Management of Atrial Fibrillation, 1997 pp. 257-279.

Haissaguerre et al., "Right and Left Atrial Radiofrequency Catheter Therapy of Paroxysmal Atrial Fibrillation," Journal of Cardiovascular Electrophysiology, 1996;7(12):1132-1144.

Haissaguerre et al., "Role of Catheter Ablation for Atrial Fibrillation," Current Opinion in Cardiology, 1997;12:18-23.

Kawaguchi et al., "Risks and Benefits of Combined Maze Procedure for Atrial Fibrillation Associated with Organic Heart Disease," JACC, 1996;28(4):985-990.

Cox, et al., "Perinodal cryosurgery for atrioventricular node reentry tachycardia in 23 patients," Journal of Thoracic and Cardiovascular Surgery, 99:3, Mar. 1990, pp. 440-450.

Cox, "Anatomic-Electrophysiologic Basis for the Surgical Treatment of Refractory Ischemic Ventricular Tachycardia," Annals of Surgery, Aug. 1983; 198:2;119-129.

Williams, et al., "Left atrial isolation," J Thorac Cardiovasc Surg; 1980; 80: 373-380.

Scheinman, "Catheter-based Techniques for Cure of Cardiac Arrhythmias," Advances in Cardiovascular Medicine, 1996, ISSN 1075-5527, pp. 93-100.

Sueda et al., "Efficacy of a Simple Left Atrial Procedure for Chronic Atrial Fibrillation in Mitral Valve Operations," Ann Thorac Surg, 1997;63:1070-1075.

* cited by examiner

ABLATION SYSTEM AND METHOD OF USE

CROSS-REFERENCE TO RELATED APPLICATIONS

This application is a continuation-in-part of U.S. patent application Ser. No. 10/364,553, filed Feb. 11, 2003 now U.S. Pat. No. 6,989,010, which is a continuation-in-part application of U.S. patent application Ser. No. 10/132,379, filed Apr. 24, 2002, now U.S. Pat. No. 6,648,883, which claims priority to Provisional U.S. Patent Application Ser. No. 60/287,202, filed Apr. 26, 2001, by Francischelli et al.

FIELD OF THE INVENTION

The present invention relates to tissue ablation devices generally and relates more particularly to devices adapted to ablate lines of tissue, for example for use in conjunction with an electrosurgical version of the Maze procedure.

BACKGROUND OF THE INVENTION

The Maze procedure is a surgical intervention for patients with chronic atrial fibrillation (AF) that is resistant to other medical treatments. The operation employs incisions in the right and left atria which divide the atria into electrically isolated portions which in turn results in an orderly passage of the depolarization wave front from the sino-atrial node (SA Node) to the atrial-ventricular node (AV Node) while preventing reentrant wave front propagation. Although successful in treating AF, the surgical Maze procedure is quite complex and is currently performed by a limited number of highly skilled cardiac surgeons in conjunction with other open-heart procedures. As a result of the complexities of the surgical procedure, there has been an increased level of interest in procedures employing electrosurgical devices or other types of ablation devices, e.g. thermal ablation, microwave ablation, cryo-ablation or the like to ablate tissue along pathways approximating the incisions of the Maze procedure. Electrosurgical systems for performing such procedures are described in U.S. Pat. No. 5,916,213, issued to Hiassaguerre, et al. U.S. Pat. No. 5,957,961, issued to Maguire, et al. and U.S. Pat. No. 5,690,661, all incorporated herein by reference in their entireties. Cryo-ablation systems for performing such procedures are described in U.S. Pat. No. 5,733,280 issued to Avitall, also incorporated herein by reference in its entirety.

In conjunction with the use of electrosurgical ablation devices, various control mechanisms have been developed to control delivery of ablation energy to achieve the desired result of ablation, i.e. killing of cells at the ablation site while leaving the basic structure of the organ to be ablated intact. Such control systems include measurement of temperature and impedance at or adjacent to the ablation site, as are disclosed in U.S. Pat. No. 5,540,681, issued to Struhl, et al., incorporated herein by reference in its entirety.

Additionally, there has been substantial work done toward assuring that the ablation procedure is complete, i.e. that the ablation extends through the thickness of the tissue to be ablated, before terminating application of ablation energy. This desired result is some times referred to as a "transmural" ablation. For example, detection of a desired drop in electrical impedance at the electrode site as an indicator of transmurality is disclosed in U.S. Pat. No. 5,562,721 issued to Marchlinski et al, incorporated herein by reference in its entirety. Alternatively, detection of an impedance rise or an impedance rise following an impedance fall are disclosed in U.S. Pat. No. 5,558,671 issued to Yates and U.S. Pat. No. 5,540,684 issued to Hassler, respectively, also incorporated herein by reference in their entireties.

Three basic approaches have been employed to create elongated lesions using electrosurgical devices. The first approach is simply to create a series of short lesions using a contact electrode, moving it along the surface of the organ wall to be ablated to create a linear lesion. This can be accomplished either by making a series of lesions, moving the electrode between lesions or by dragging the electrode along the surface of the organ to be ablated and continuously applying ablation energy, as described in U.S. Pat. No. 5,897,533 issued to Mulier, et al., incorporated herein by reference in its entirety. The second basic approach to creation of elongated lesions is simply to employ an elongated electrode, and to place the elongated electrode along the desired line of lesion along the tissue. This approach is described in U.S. Pat. No. 5,916,213, cited above and. The third basic approach to creation of elongated lesions is to provide a series of electrodes and arrange the series of electrodes along the desired line of lesion. The electrodes may be activated individually or in sequence, as disclosed in U.S. Pat. No. 5,957,961, also cited above. In the case of multi-electrode devices, individual feedback regulation of ablated energy applied via the electrodes may also be employed. The present invention is believed useful in conjunction with all three approaches.

SUMMARY OF THE INVENTION

The present invention is directed toward an improved system for creating lesions and assessing their completeness or transmurality. In particular, the preferred embodiments of the invention are directed toward an improved system for creating elongated lines of lesion and assessing their completeness or transmurality. In the preferred embodiment as disclosed, the apparatus for producing the lesions is an electrosurgical device, in particular a saline-irrigated bipolar electrosurgical forceps. However, the mechanism for assessing lesion transmurality provided by the present invention is believed useful in other contexts, including unipolar radiofrequency (RF) ablation and RF ablation using catheters or hand-held probes. The mechanism for assessing transmurality may also be of value in the context of other types of ablation systems, particularly those which ablation occurs in conjunction with an induced rise in tissue temperature such as those applying ablation energy in the form of microwave radiation, light (laser ablation) or heat (thermal ablation).

According to the present invention, assessment of transmurality of a lesion is accomplished by monitoring the impedance of the tissue to be ablated. The inventors have determined that, particularly in the case of a saline-irrigated electrosurgical ablation device, tissue impedance first falls and then reaches a stable plateau, during which portion the lesion is completed. Thereafter, the impedance rises. Rather than attempting to detect a desired drop or a desired increase impedance as described in the above cited Yates, Hassler and Marchlinski patents, the present invention detects completeness of a lesion in response to the measured impedance remaining at a stable level for a desired period of time, hereafter referred to as an impedance plateau. In the context of RF ablation, measurement of impedance may be done using the ablation electrodes or may be done using dedicated electrodes adjacent to the ablation electrodes. In the context of the other types of ablation discussed above, impedance measurement would typically be accomplished by means of a dedicated set of impedance measurement electrodes.

In the context of RF ablation, the invention is believed most valuable in the conjunction with an ablation device having multiple, individually activatable electrodes or electrode pairs to be arranged along a desired line of lesion. In this context, the mechanism for determining transmurality of lesions adjacent individual electrodes or pairs may be used to deactivate individual electrodes or electrode pairs, when the lesions in tissue adjacent these individual electrodes or electrode pairs are complete. This allows the creation of an essentially uniform lesion along the line of electrodes or electrode pairs, regardless of differences in tissue thickness adjacent the individual electrodes or electrode pairs. However, the invention is also believed useful in conjunction with assessment of transmurality of lesions produced by devices having only a single electrode or single electrode pair. Similar considerations apply to the use of the present invention in the contexts of other types of ablation as listed above.

In yet another aspect of the invention, RF power delivery can also be controlled in order to assess lesion transmurality. The ablation will commence at a first power level and will be increased to a second power level as certain conditions are satisfied. The power level can also be increased from the second power level to a third power level as certain conditions are satisfied. The increase in power level can continue in the same stepwise manner, increasing the power level from an N power level to an n+1 power level until a set of conditions are met that indicates that transmurality has been achieved and/or that the power should be turned off. Conditions for an increase in power level can include one or more of: the detection of a plateau in impedance or the achievement of a maximum permitted time for that power level. Conditions indicating that transmurality has been achieved can include one of: the lack of change in detected impedance in response to the change in power level or the detection of a rapid rise in impedance. If transmurality is detected by satisfying one of these conditions, the power is turned off and the ablation is complete. If a condition indicating that transmurality has been achieved is not detected, such as a drop in detected impedance in response to the change to the higher power level, ablation is continued at the higher power level until the conditions are met for again increasing the power level or conditions indicating transmurality are met. This process may be continued in a stepwise fashion until the conditions for detection of transmurality are detected, a predetermined number of plateaus in impedance have been detected or until an overall maximum time for the ablation is achieved.

In yet another aspect of the invention, complete or partial submersion in a fluid of the ablating portion of an ablation device may be detected prior to, during or following an ablation procedure. During an ablation procedure one or more fluids, such as blood, CPB fluids and/or surgical field irrigation fluids, can collect or pool in the atria and/or pericardial sac. When the ablation device is positioned and/or clamped onto tissue, a portion of the device, such as one or more ablating elements of the device, may become fully or partially submerged by these fluids. One or more submersion sensors positioned on the device can be used to detect and monitor the submersion of at least a portion of the device. Since total submersion, oscillating submersion, or partial submersion of one or more ablating elements, e.g., ablation electrodes, can cause, for example, impedance changes and affect the ablation cycle and lesion quality, different power or ablating energy and transmurality algorithms may be applied for the various degrees of submersion.

DETAILED DESCRIPTION PREFERRED EMBODIMENTS

Figure 1:
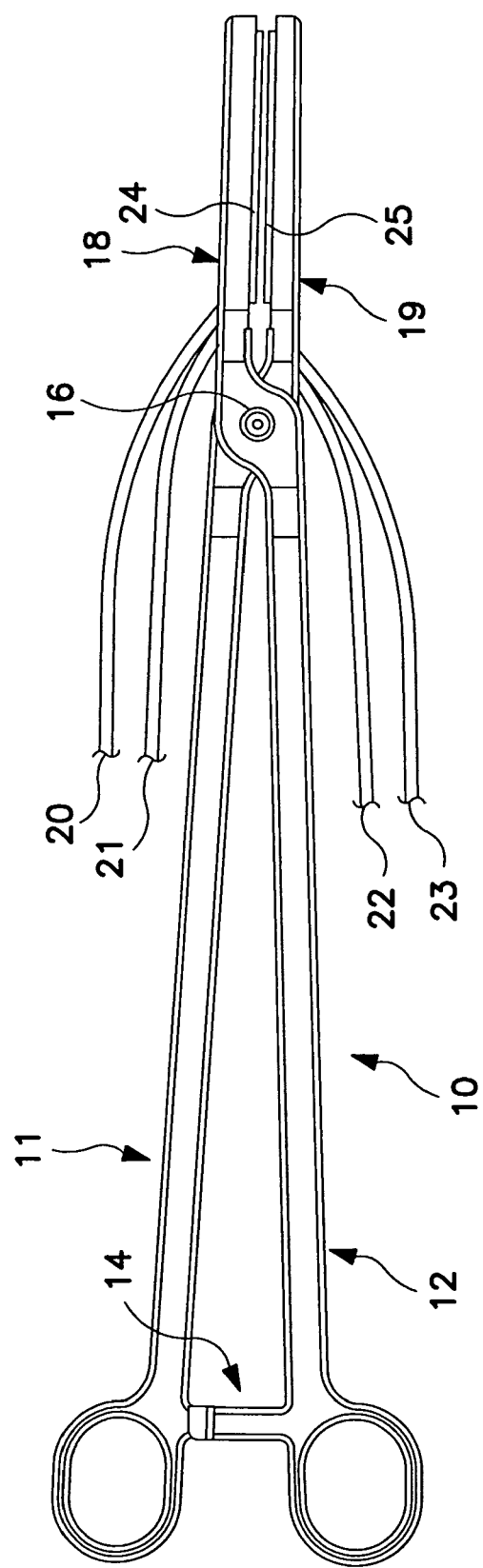
FIG. 1 is a plan view of a type of electrosurgical hemostat that may be used in conjunction with the present invention.

FIG. 1 is a plan view of a bipolar, saline irrigated electrosurgical hemostat of a type that may be employed in conjunction with the present invention. The hemostat is provided with elongated handles 11 and 12 and a lock mechanism 14, similar to a conventional surgical hemostat. The handles are connected to one another by pivot or hinge 16, and continue distally in the form of elongated jaws 18 and 19. Jaws 18 and 19 carry an elongated electrode or series of electrodes 24, 25, respectively, to which ablation energy, e.g. RF energy is applied by means of conductors 21 and 22. The electrodes are adapted to be irrigated by a saline solution or other conductive fluid along their length, provided via inlet tubes 20 and 23. In operation, tissue to be ablated is compressed between the jaws, and RF energy is applied between the electrode or electrode sets 24 and 25, as generally described in U.S. Pat. No. 6,096,037 issued to Mulier et al incorporated herein by reference in its entirety.

Figure 2A:
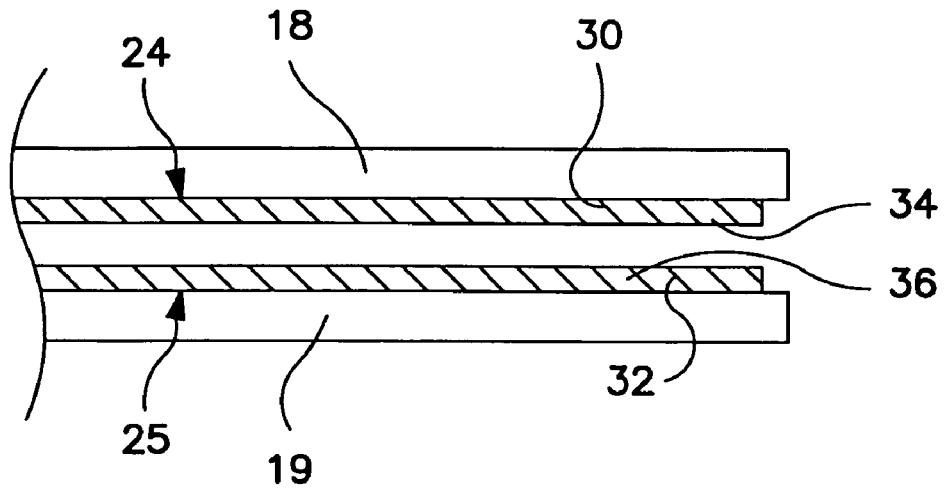
FIGS. 2a and 2b illustrate alternative electrode configurations for a hemostat generally according to FIG. 1.

FIG. 2a shows a first embodiment of an electrode arrangement for a hemostat generally as illustrated in FIG. 1. Illustrated components correspond to identically numbered components in FIG. 1. In this embodiment, electrodes 24 and 25 take the form of elongated coil electrodes 30 and 32, mounted around porous tubes 34 and 36, through which saline or other conductive fluid is delivered. The arrangement of the electrodes may also be reversed, for example placing coils 30 and 32 within elongated porous tubes 34 and 36, to accomplish a similar result. Alternatively, any other arrangement for providing an elongated electrode and delivery of saline solution along the length thereof may be substituted. The particular configuration of the electrode is not critical to the present invention. For example, irrigated electrodes corresponding to those described in U.S. Pat. No. 6,096,037 issued to Mulier, et al., U.S. Pat. No. 5,876,398 issued to Mulier, et al., U.S. Pat. No. 6,017,378 issued to Brucker, et al or U.S. Pat. No. 5,913,856 issued to Chia, et al., all incorporated herein by reference in their entireties may also be substituted. It should also be noted that while the electrode system as illustrated in FIG. 2a is a bipolar system, the invention may also be employed in conjunction with unipolar electrodes and/or in the form of a probe or a catheter. In some embodiments, irrigation of the electrodes may be omitted.

Figure 2B:
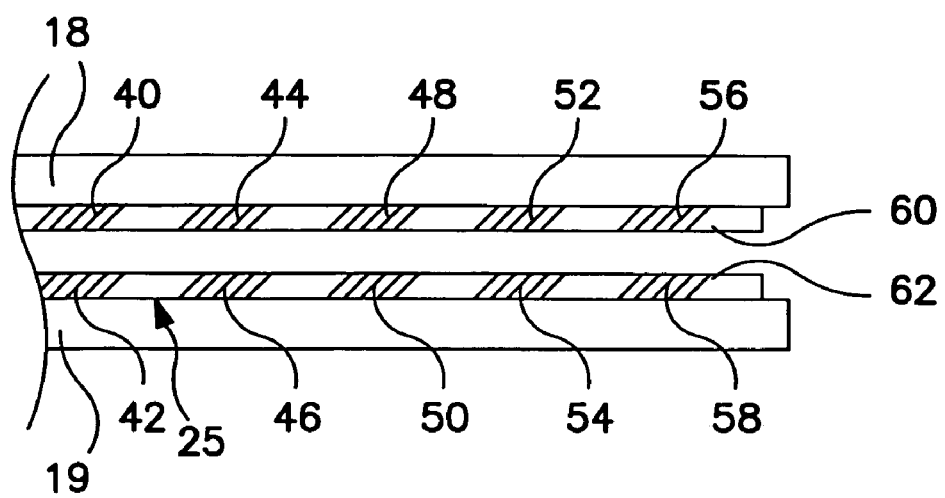

FIG. 2b illustrates an alternative embodiment of an electrode system for a hemostat generally as illustrated in FIG. 1. In this case, rather than a single pair of electrodes, multiple electrode pairs are provided. The electrode pairs comprise coil electrodes 40 and 42, 44 and 46, 48 and 50, 52 and 54, and 56 and 58. However, other pairings of electrodes might also be substituted, for example, pairing electrodes 40 and 44, electrodes 48 and 52 or the like. In this embodiment, the electrode pairs are mounted around porous plastic tubes 60 and 62 through which saline or other electrically conductive fluid is delivered. As in the case with the embodiment of FIG. 2a, the arrangement of these electrodes may readily be reversed, placing the electrodes within the lumen of plastic tube 60 or 62 and any other arrangement providing multiple, irrigated electrodes may also be substituted. As in the case of the embodiment of FIG. 2a, unipolar electrodes might be substituted for the multiple bipolar pairs as illustrated and/or the invention may be practiced in conjunction with a multi-electrode probe or catheter. While the particular arrangement of electrodes is not believed critical to practicing the present invention, it is believed that the invention may be most beneficially practiced in conjunction with a set of linearly arranged bipolar electrode pairs as illustrated in FIG. 2b.

In use, the hemostat is arranged so that the tissue to be ablated is located between the jaws 18 and 19, and pressure is applied in order to compress the tissue slightly between the jaws to ensure good electrical contact. All electrode pairs may be activated individually and may be individually deactivated when the lesions between the individual electrode pairs are completely transmural. Alternatively, electrode pairs could be activated sequentially, with one pair deactivated upon a detection of a complete lesion between the electrode pair, followed by activation of the next sequential electrode pair. Corresponding use of the invention in conjunction with a series of unipolar electrodes, for example corresponding to electrodes along one of the two jaws in conjunction with a remote ground plate or a similar series of individually activatable electrodes on a catheter or probe in conjunction with a ground plate is also possible.

Figure 3:
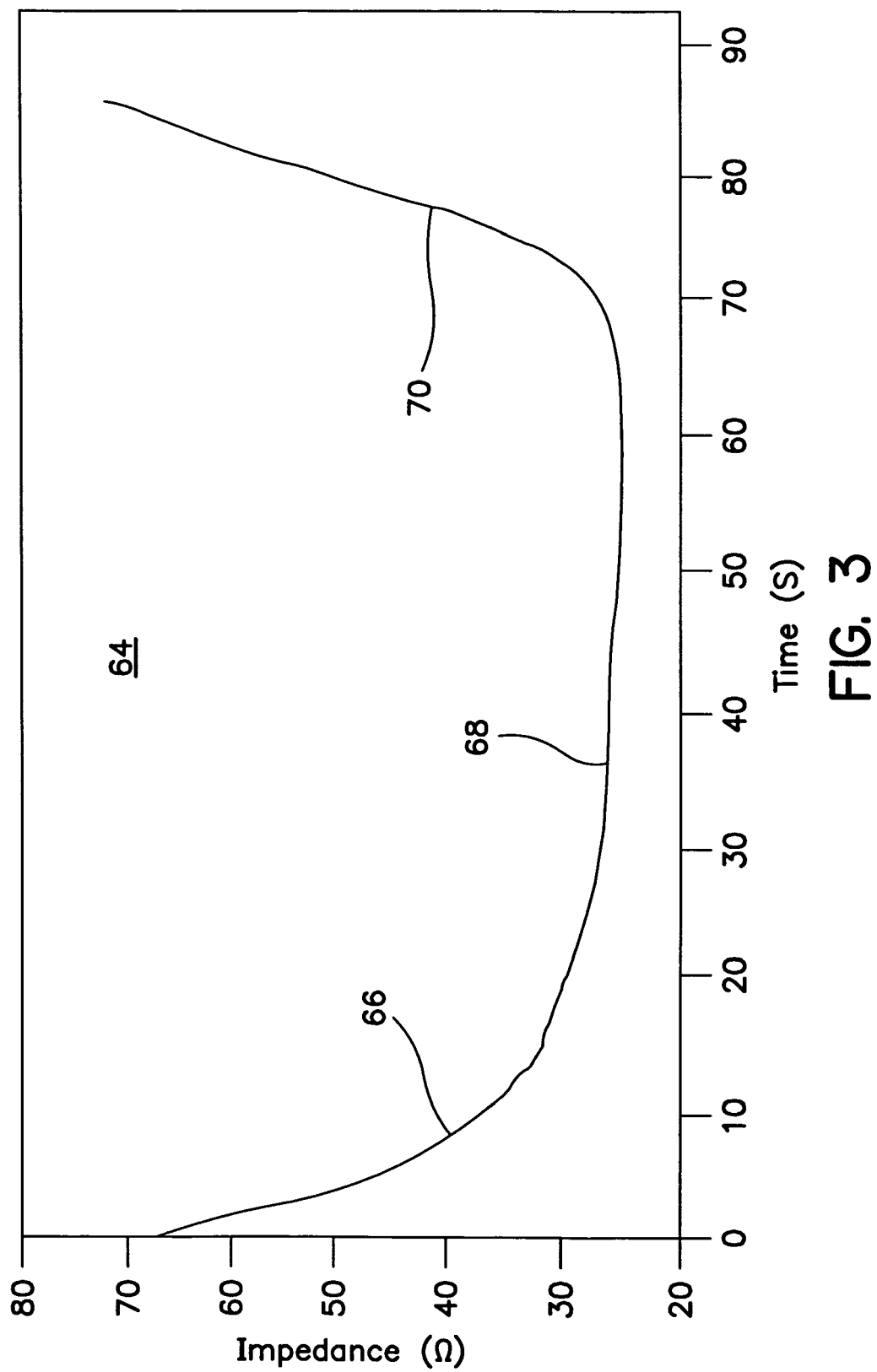
FIG. 3 illustrates the fall and plateau of impedance measured across tissue ablated using a bi-polar, saline irrigated electro surgical hemostat.

FIG. 3 is a graph 64 illustrating measured impedance versus time across tissue located between the electrodes of an irrigated bipolar hemostat 10 as illustrated in FIG. 1. FIG. 3 illustrates the drop in impedance 66 followed by an impedance plateau 68, ultimately followed by an impedance rise 70. The impedance plateau 68 is the primary indicator of transmurality employed by the present invention. Following the impedance plateau 68, as tissue is desiccated or as steam or microbubbles forms in the tissue, an impedance rise 70 will generally occur. In some embodiments of the invention, the detection of this rise in impedance 70 is employed as an alternative or mechanism for assessing transmurality and/or as a safety mechanism in order to assure shut off of the ablation electrodes before excessive physical damage to the tissue results.

Figure 4:
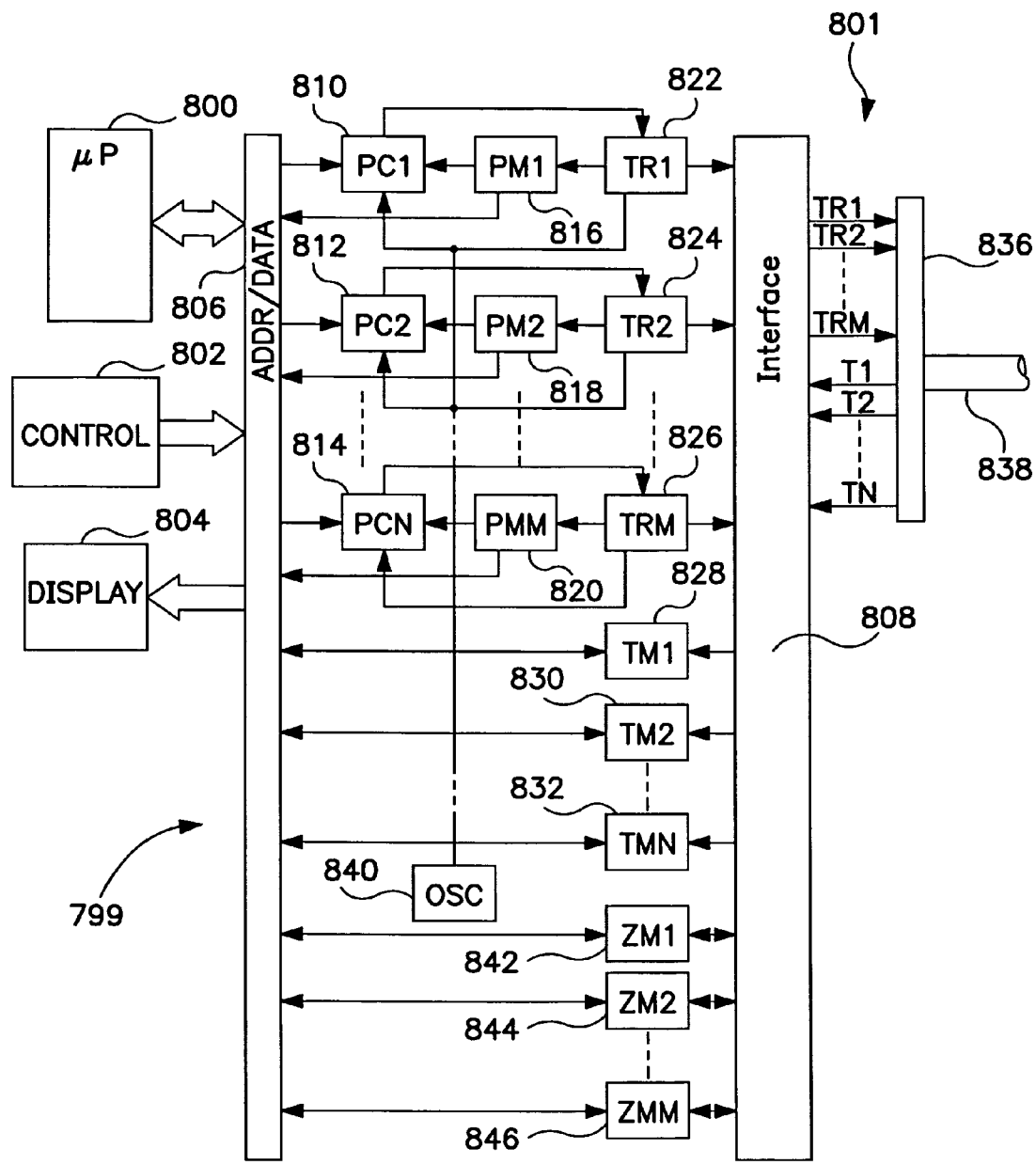
FIG. 4 is a functional block diagram of an RF generator appropriate for use in practicing the present invention, particularly adapted for use in conjunction with an ablation system employing multiple, individually activatable electrodes or multiple electrode pairs.

FIG. 4 is a functional block diagram illustrating one embodiment of an RF generator system 799 for use in conjunction with the present invention. In this embodiment, separately controllable RF outputs are provided for individual ablation electrodes or electrode pairs on an associated RF ablation device, for example as in FIG. 2B. The RF generator could of course also be used with ablation devices having only a single electrode or electrode pair as in FIG. 2A. With the exception of the electrogram amplitude measurement circuits discussed below, the generator 799 corresponds generally to that described in conjunction with FIG. 14 of the '961 patent issued to Maguire, et al., cited above. The RF generator disclosed in the '961 patent provides feedback control of RF power based upon either measured power (constant power) or temperature. The present invention is somewhat easier to implement in conjunction with the constant power mode, but may also be adapted to a temperature-regulated mode or to other feedback power regulation mechanism.

Display 804 and controls 802 are connected to a digital microprocessor 800, which permits interface between the user and the remainder of the electrical components of the system. Microprocessor 800 operates under control of stored programming defining its operation including programming controlling its operation according to the present invention, as discussed in more detail below. Microprocessor 800 provides control outputs to and receives input signals from the remaining circuitry via address/data bus 806. In particular, the microprocessor 800 provides for monitoring of power, current, voltage, impedance and temperature. As necessary, the microprocessor will provide this information to the display 804. Additionally, the microprocessor 800 permits the user to select the control mode (either temperature or power) and to input the power set point, temperature set point, and a timer set point to the system. The primary source of power for the radio-frequency generator may be a 12 V battery rated at 7.2 ampere-hours. Alternatively, the device may be AC powered. A back-up battery (not shown) such as a lithium cell may also be provided to provide sufficient power to the microprocessor 800 to maintain desired memory functions when the main power is shut off.

The power supply system as illustrated includes a desired number "M" of individually controllable RF power supplies and receives temperature inputs from a desired number "N" of temperature sensing devices in the ablation device, illustrated schematically at 836 and receives temperature inputs from a desired number "M" of impedance monitoring circuits. Each RF power supply includes a transformer (822, 824, 826), a power control circuit (810, 812, 814) and a power measurement circuit (816, 818, 820). A crystal-locked radio-frequency oscillator 840 generates the switching pulses, which drive both the power transformers (822, 824, 826) and the power controllers (810, 812, 814). Power controllers (810, 812, 814) may be analog controllers which operate by pulse-width modulation by comparing a power set point signal from microprocessor 800 with an actual power signal generated by a power measurement circuit (816, 818, 820), which may, for example, include a torroidal transformer coupled to the power output from the associated transformer (822, 824, 826). The power measurement circuits (816, 818, 820) multiply the output current and voltage and provide the resulting actual power signal to both the power controllers (810, 812, 814) and the microprocessor 800.

The RF power output of the transformers (822, 824, 826) is provided to inter face board 808, and thereby is provided to the ablation electrode or electrodes on the ablation device 838. Separate analog comparator circuits (not illustrated) may also be provided for monitoring the output of the power measurement circuits (816, 818, 820), in order to shut-off current to the output transformers (822, 824, 826) if the power exceeds a limit, typically 55 watts. Power transformers (822, 824, 826) may include center taps, which receive the outputs of the power controllers (810, 812, 814). Secondary windings of the transformers (822, 824, 826) may provide for continuous monitoring of the applied voltage in order to permit the power calculations by power measurement circuits (816, 818, 820).

The illustrated power RF generator system 799 employs software controlled temperature processing, accomplished by microprocessor 800, which receives the "N" temperature input signals from temperature measurement circuits (828, 830, 832), each of which are coupled to a corresponding temperature sensor in ablation device 838 by means of an electrical connector, illustrated schematically at 836 and interface board 808. If programmed to operate in the temperature controlled mode, processor 800 receives the "N" temperature signals and, based upon the indicated temperatures, defines power set points for each of the power control circuits (810, 812, 814), which in the manner described above control the power levels applied to electrodes on the ablation device through interface 808. Processor 800 may also selectively enable or disable any of the "M" provided RF power supplies, in response to external control signals from controls 802 or in response to detected anomalous temperature conditions.

In addition to the circuitry as described above and disclosed in and disclosed in the Maguire, et al. '961 patent, the apparatus of FIG. 4 includes multiple impedance monitoring circuits ZM1, ZM2 . . . ZMM (842, 844 and 846 respectively), which may operate as described in U.S. Pat. No. 5,733,281, issued to Nardella, or U.S. Pat. No. 5,863,990, issued to Li, also both incorporated herein by reference in their entireties to measure an impedance between electrodes on a RF ablation device. Impedance may be measured between the ablation electrodes or between electrodes located adjacent the ablation electrodes, as described in U.S. Pat. No. 5,558,671, incorporated by reference above. Individual impedance measurements made by measurement circuits 842, 844 and 846 are provided to the address/data bus 806 and thence to microprocessor 800 for analysis to determine whether the impedance over time, indicates that the lesion associated with the measured impedance is completely transmural. As discussed in more detail below, a determination of transmurality is made in response to a detection of a series of impedance measurements that are relatively constant, over a desired period of time or over a defined number of successive impedance measurements. In some embodiments, an abrupt rise in impedance may also be employed to terminate delivery of ablation energy.

As an alternative to dedicated impedance monitoring circuits, the microprocessor may employ voltage and current measurements of impedance measurement signals generated by the power transformers (822, 824, 826) to derive impedance and may use such derived impedance values in conjunction with the present invention. For example, measurement of impedance in this fashion is disclosed in U.S. Pat. No. 5,540,681, issued to Struhl, et al, cited above or U.S. Pat. No. 5,573,533, issued to Struhl, also incorporated herein by reference in its entirety.

In cases in which an alternative ablation energy generation apparatus is employed, particularly those in which a rise in tissue temperature is induced, e.g. laser, microwave or thermal ablation, the RF generation circuitry of FIG. 4 would be replaced with a corresponding alternative ablation energy generation apparatus. The measurement of tissue impedance and its use according to the present invention, however, may still be useful in conjunction with these alternative ablation energy generation systems.

Figure 5A:
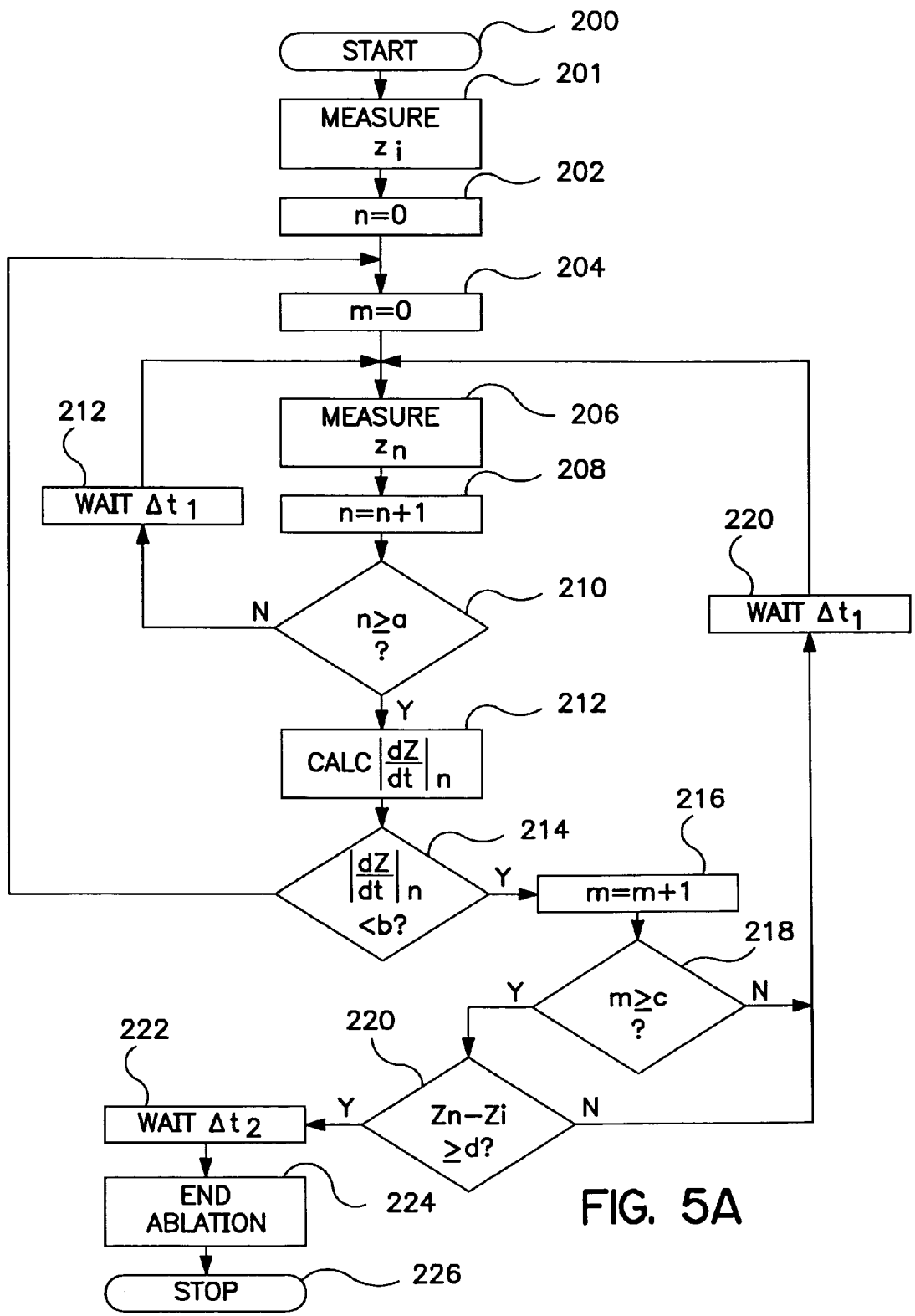
FIG. 5a is a functional flow chart illustrating a first mode of operation of the device illustrated in FIG. 4 in practicing the present invention.

FIG. 5A is a functional flow chart illustrating the operation of a device as in FIG. 4, according to the present invention. The flow chart of FIG. 5A illustrates operation of the device of FIG. 4 to control provision of RF energy to an individual electrode or electrode pair. In the event that multiple electrodes or electrode pairs are employed, the control methodology of FIG. 5A would be applied to each electrode or electrode pair individually, as discussed in more detail below in conjunction with FIGS. 7 and 8.

The flow chart of FIG. 5A illustrates a method of assessing transmurality and terminating delivery of ablation energy to an electrode or an electrode pair responsive to detection of a plateau in impedance in conjunction with a detected drop in impedance. Following the detection of a plateau in conjunction with the required impedance drop, the device waits a defined time period and then terminates the application of ablation energy to the associated electrode pair. Measurement of impedance in tissue associated with the electrode pair may be made using the ablation electrodes themselves or electrodes located in proximity to the ablation electrodes, for example as described in the Yates '671 patent, incorporated by reference above.

After initialization at 200, the microprocessor 800 (FIG. 4) initiates delivery of ablation energy at 201 and causes the impedance measurement circuitry associated with the electrode or electrode pair being evaluated or derives impedance based on applied voltage and current as discussed above to acquire a base line or initial impedance $Z_i$, which may be, for example the maximum impedance during the first three seconds of ablation. At 202 and 204 counts "n" "m" are reset to zero. The microprocessor thereafter acquires a current impedance value $Z_n$ at 206. The value of "n" is incremented at 208 and compared with a predefined value "a" at 210 to determine whether a sufficient number of impedances have been measured in order to calculate the rate of change of impedance (dZ/dt). For example, dZ/dt may be calculated by taking the measured impedance $Z_n$ and comparing it to the preceding measured impedance $Z_{n-1}$, in which case n would have to be greater or equal to 2 in order for dZ/dt to be calculated. Alternatively, dZ/dt may be calculated by taking the measured impedance $Z_n$ and comparing it to the previously measured impedance $Z_{n-2}$, in which case n would have to be greater or equal to 3 in order for dZ/dt to be calculated. If "n" is less than "a" at 210, the microprocessor waits an impedance sampling interval $\Delta t_1$ which may be, for example, 0.2 seconds, and then triggers an impedance measurement again at 206. This process continues until there are a sufficient number of collected impedance measurements to calculate dZ/dt at 212.

At 212, the microprocessor 800 employs the stored impedance measurements to calculate dZ/dt, which may, for example, be calculated as equal to $(1/(2\Delta t_1))(Z_n - Z_{n-2})$. The absolute value of dZ/dt, i.e., $|dZ/dt|_n$ is employed to assess whether or not an impedance plateau has been reached at 214. The microprocessor checks at 214 to determine whether $|dZ/dt|_n$ is less than a defined constant b, indicative of a minimal rate of change of impedance. In the case of an elongated, fluid irrigated ablation electrode similar to that illustrated in FIG. 2A, for example using an electrode of approximately 5 centimeters in length operated in a constant power mode with a power of less than 27 watts, an appropriate value of "b" might be 1.3. For other electrode configurations and other power levels, the value of "b" may have to be adjusted. Other power control modes, e.g. temperature controlled would similarly require adjustment of this parameter. The value of "b" and other parameters employed to determine transmurality using the present invention can be determined empirically in the laboratory by applying the specific electrode set and RF generation system in question to test specimens, reading impedances at defined sample intervals and using the results to optimize the various parameters.

In the event that $|dZ/dt|_n$ is sufficiently small in value at 214, the count "m" is incremented at 216 and m is compared to a third constant "c" which sets forth the defined number of low value $|dZ/dt|_n$ measurements required to detect an impedance plateau. For example, in a system as described herein, "c" may be 6-12. Alternatively, rather than requiring an entire series of measured $|dZ/dt|_n$ values to be less than "b", a requirement that a defined proportion of the $|dZ/dt|_n$ values must be less than "b" may be substituted, e.g. 8 of 12, or the like.

If the number of low values of $|dZ/dt|_n$ is less than "c" at 218, the microprocessor waits the impedance sampling interval $\Delta t_1$ at 220 and continues to acquire successive impedance measurements until sufficient number of sequential low values of $|dZ/dt|_n$ have occurred at 218. At that point, the microprocessor then compares the current impedance value Zn with the initial impedance value $Z_i$ to determine whether a sufficient impedance drop "d" has occurred. If not, the microprocessor waits for the next impedance sampling interval at 220 and continues to collect impedance measurements and make calculations of $|dZ/dt|_n$ until such time as an impedance plateau is recognized at 218 and a sufficient impedance drop is recognized at 220. When both of these criteria have been met at 220, the microprocessor than waits for an additional time interval $\Delta_{t2}$ to assure completeness of the lesion at 222 and thereafter terminates the provision of ablation energy to the specific electrode pair being regulated at 224 and the ablation process with regard to that electrode or electrode pair is terminated at 226.

Figure 5B:
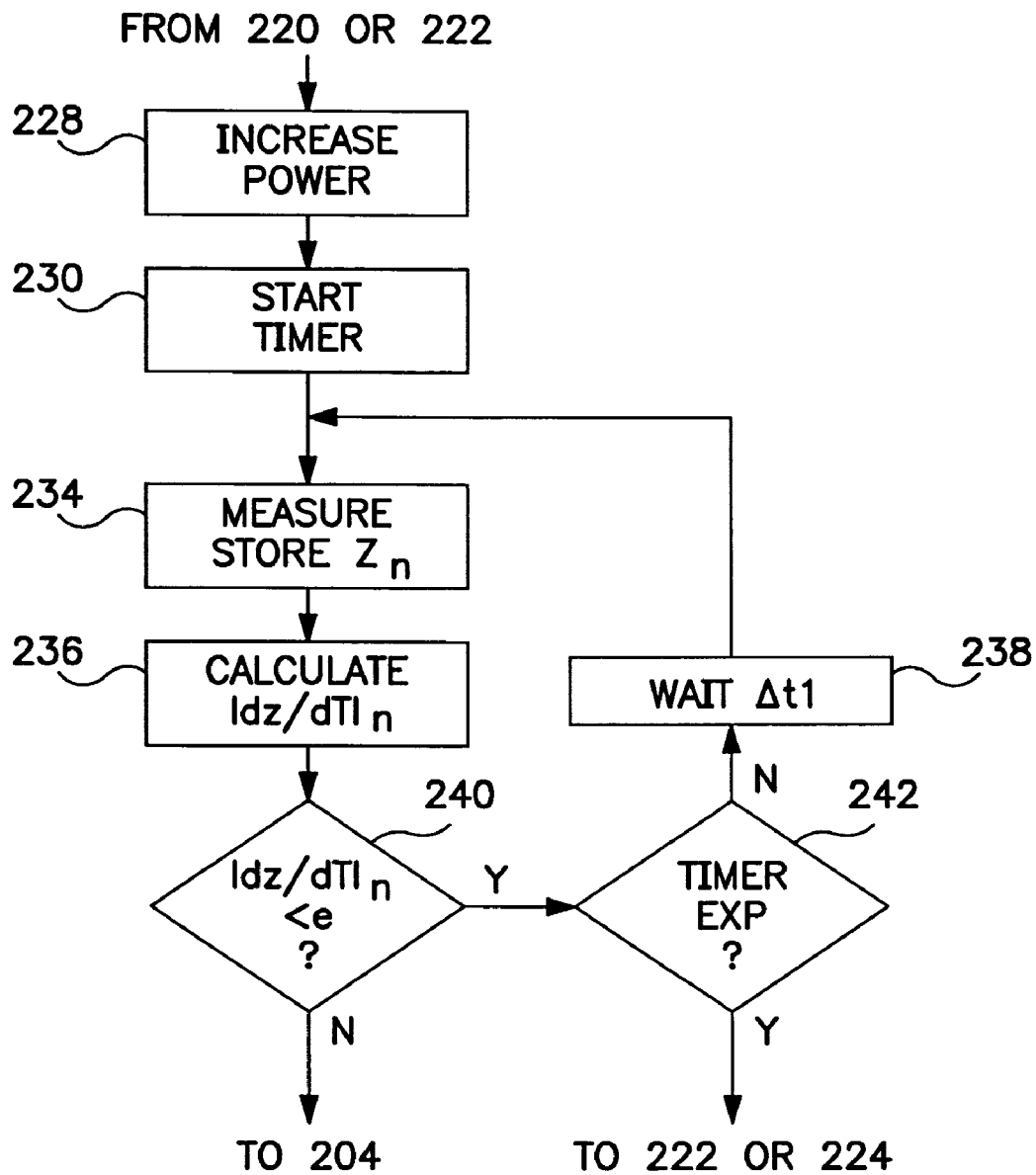
FIG. 5b illustrates an alternative mode of operation of a device as in FIG. 4 in practicing the present invention.

FIG. 5B illustrates an additional set of operations for implementing a transmurality measurement method generally as in FIG. 5A. The operations of FIG. 5B may either be substituted for step 222 of FIG. 5A or alternatively may be performed before or after step 222. In the additional operations illustrated in FIG. 5B, the microprocessor increases the power to the electrodes under consideration slightly at 228 and sets a timer at 230. The microprocessor then causes the impedance measurement apparatus associated with the electrodes under consideration to measure current impedance at 234 and calculate $|dZ/dt|_n$ at 236, in the same fashion as discussed above. In the event that the value of $|dZ/dt|_n$ is greater then a defined constant "e" at 240, the microprocessor returns to 204 and resets the value of "m" to zero, essentially reinitializing the search for an impedance plateau. The value of "e" may be equal to "b" or may be different. If the value of $|dZ/dt|_n$ is sufficiently small at 240, the microprocessor checks at 242 to determine whether the timer has expired. If not, the microprocessor waits the impedance sampling interval $\Delta t_1$ at 238 and continues to collect impedance values and calculate $|dZ/dt|_n$ values until expiration of the timer at 242, at which point it either terminates ablation at 224 or initiates the waiting period $\Delta t_2$ at 222.

Figure 6:
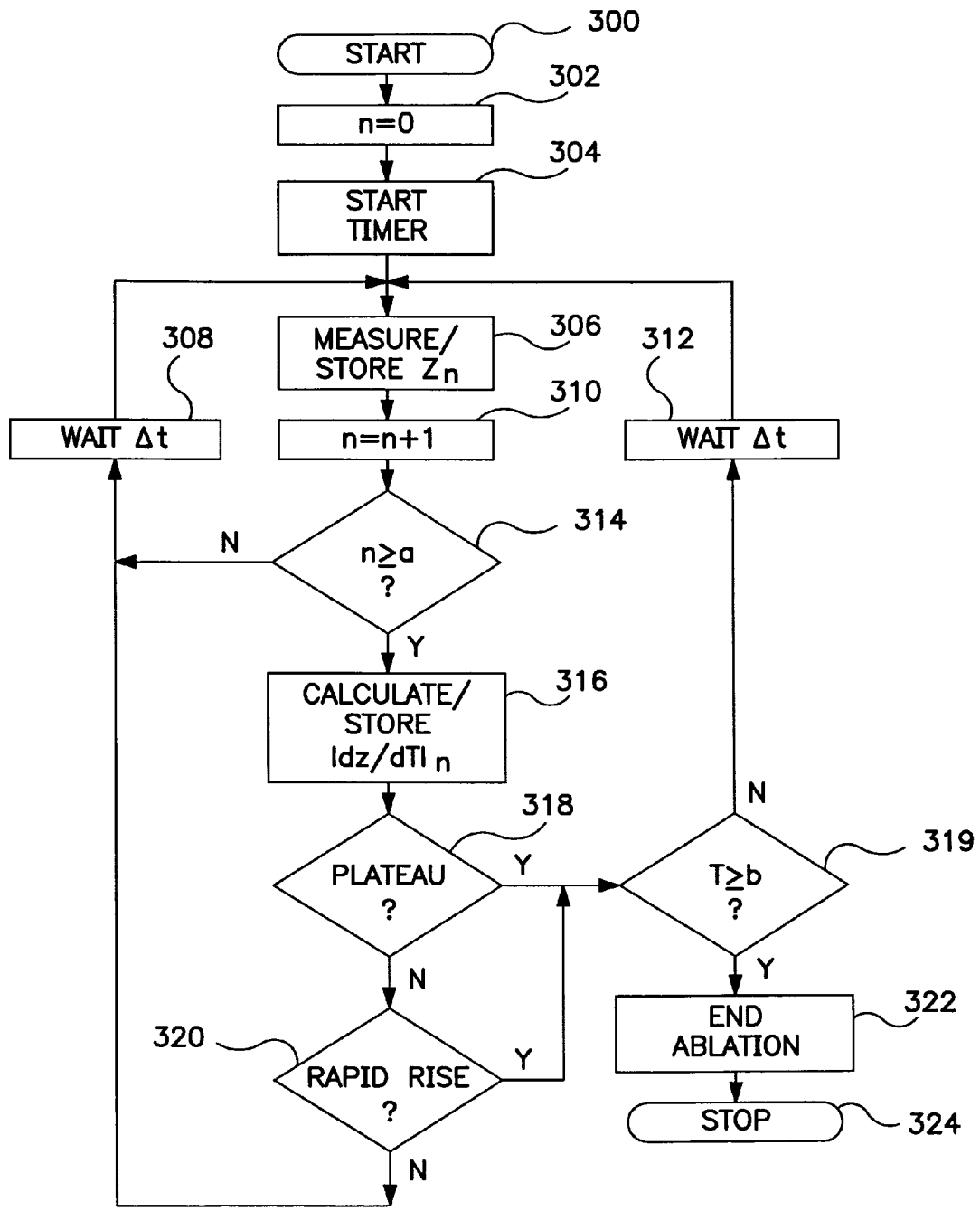
FIG. 6 illustrates an additional alternative mode of operation of a device as in FIG. 4 in practicing the present invention.

FIG. 6 illustrates a second basic approach to assessment of transmurality and control of delivery of ablation energy to an electrode pair. In the same fashion as for FIGS. 5a and 5b, the procedure defined by the flow chart of FIG. 6 should be understood to be employed in conjunction with an impedance measurement circuit with a single electrode pair, which procedure would be repeated for other electrodes or electrode pairs, if present. After initiation at 300, the value of "n" is set to zero at 302 and a timer is initiated at 304, used to determine that a sufficient amount of time has passed prior to termination of ablation. For example, in the context of a bipolar irrigated hemostat similar to FIGS. 1 and 2a as described above, having electrode lengths of 2 to 5 centimeters and receiving RF energy at a level of 27 watts or less, ten seconds may be an appropriate time interval for the timer initiated at 304.

The microprocessor than measures the current impedance $Z_n$ at 306, increments the value of "n" at 310 and checks at 314 to determine whether an adequate number of impedance measurements have been accumulated to make a calculation of dZ/dt at 314, in the same fashion as discussed above in conjunction with FIGS. 5a and 5b. If an inadequate number of samples have been collected, the microprocessor waits the impedance sampling interval $\Delta t$ at 308 and continues to collect impedance measurements until an adequate number "a" of measurements have been collected. In the specific example presented, "a" may be set equal to 5 and $\Delta t$ may be 0.2 seconds. After an adequate number of impedance measurements have been collected at 314, the microprocessor calculates the value of $dZ/dt_n$ and $|dZ/dt|_n$ at 316. In conjunction with the specific mechanism of plateau detection illustrated in FIG. 6, filtered or average impedance values $Z_a$ may be employed to calculate dZ/dt and $|dZ/dt|_n$.

For example, at 316, the microprocessor may calculate the value of dZ/dt according to the following method. The microprocessor may employ a 5 point moving average filter to produce an average impedance value $Z_a$, which is equal to $(Z_n+Z_{n-1}+Z_{n-2}+Z_{n-3}+Z_{n-4})/5$. The value of $dZ/dt_n$ and $|dZ/dt|_n$ may be calculated in the same fashion as in conjunction with the flow charts of FIGS. 5A and 5B discussed above, substituting the averaged impedance values $Z_a$ for the individual impedance values $Z_n$ as employed in the previous flow charts. In this case, $dZ/dt_n$ would be $(1/(2\Delta t))(Z_n-Z_{n-2})$ and $|dZ/dt|_n$ would be the absolute value of $dZ/dt_n$.

At 318, microprocessor 800 may attempt to determine whether an impedance plateau has been reached employing the following method. The microprocessor reviews the preceding 15 measurements of $dZ/dt_n$, and $|dZ/dt|_n$ and applies three criteria to those values, all three of which must be met in order for an impedance plateau to be detected. For a fluid irrigated hemostat as described, the rules may be as follows: for n=1 to 15; $|dZ/dt|_n$ must be less than or equal to 1 for all 15; and for n=1 to 15 the value of $dZ/dt_n$ must be less than or equal to 0.75, for 13 of the 15; and for n=1 to 15, $|dZ/dt|_n$ must be less than or equal to 0.5, for 10 of the 15. If all of these criteria are met at 318, the microprocessor checks at 319 to determine whether an adequate period of time has elapsed since ablation was initiated, if not, the microprocessor waits for the impedance sampling interval $\Delta t$ at 312 and continues to measure impedances and calculate values of dZ/dt according to the above described method until both a plateau is present and the defined time period "b" has elapsed at 319. After the required time period at "b" at 319 has elapsed, delivery of ablation energy to the associated electrode or electrode pair is terminated at 322 and the ablation process ceases at 324 as to that electrode pair.

In this embodiment, in the event that an impedance plateau fails to manifest itself, the microprocessor may nonetheless safely terminate provision of ablation energy to the electrode pair under consideration in response to a detected rapid rise in impedance, which normally follows the impedance plateau. In the event that a plateau is not detected at 318, the microprocessor checks the preceding stored values of $dZ/dt_n$ to look for a rapid rise in impedance. For example, a rapid rise in impedance may be detected using the following rule: for n=1 to 10, $dZ/dt_n$ must be greater than or equal to 1.0 for all 10. If this rapid rise criteria is met at 320, the processor checks to see whether the required minimal time period has elapsed at 319, and if so, terminates ablation at 322 as discussed above. If the minimal time interval "b" has not elapsed, the microprocessor continues to acquire measurements of impedance and continues to calculate values of $dZ/dt_n$ and $|dZ/dt|_n$ until either an impedance plateau is detected at 318 or a rapid rise in impedance is detected at 320 and the minimum time interval has expired at 319.

Figure 7:
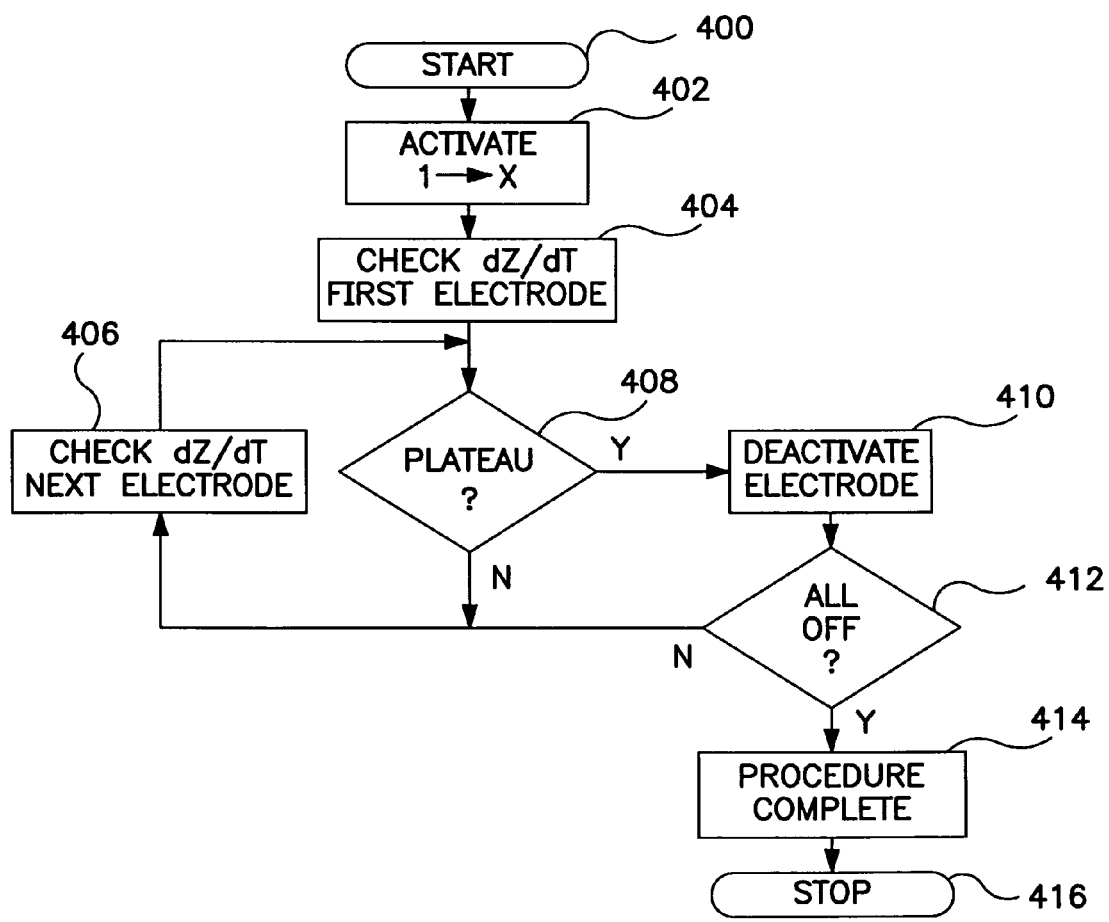
FIG. 7 illustrates a first mode of operation of a device as in FIG. 4 to activate and deactivate of individual electrodes or electrode pairs.

FIG. 7 is a function flow chart illustrating the over-all operation of the device in conjunction with a multi electrode or multi electrode pair ablation apparatus. In the flow chart of FIG. 7, all the electrodes are activated simultaneously and individual electrodes or electrode pairs are deactivated in response to impedance measurements associated with the electrode pair indicating that the lesion formed between that electrode pair is completely transmural. In this circumstance, the ablation system works as follows.

After initialization at 400, all electrodes 1-x are activated at 402, meaning that ablation energy is provided to all electrodes and electrode pairs. The microprocessor then checks the value of dZ/dt and/or |dZ/dt| at the first of the electrode pairs at 404, using any of the mechanisms discussed above in conjunction with FIGS. 5a, 5b and 6. At 408, the microprocessor checks using any of the mechanisms described above to determine whether an impedance plateau has been reached or, in the event that additional criteria for shut off of ablation energy are provided, to see whether any of these additional criteria are reached. If so, the electrode being examined is deactivated at 410 by ceasing the delivery of ablation energy to the electrode or electrode pair. If not, the microprocessor checks the value of dZ/dt and/or |dZ/dt| for the next electrode at 406. This process continues until all electrodes are deactivated at 412, after which the procedure is deemed complete at 414 and the ablation process is terminated at 416.

Figure 8:
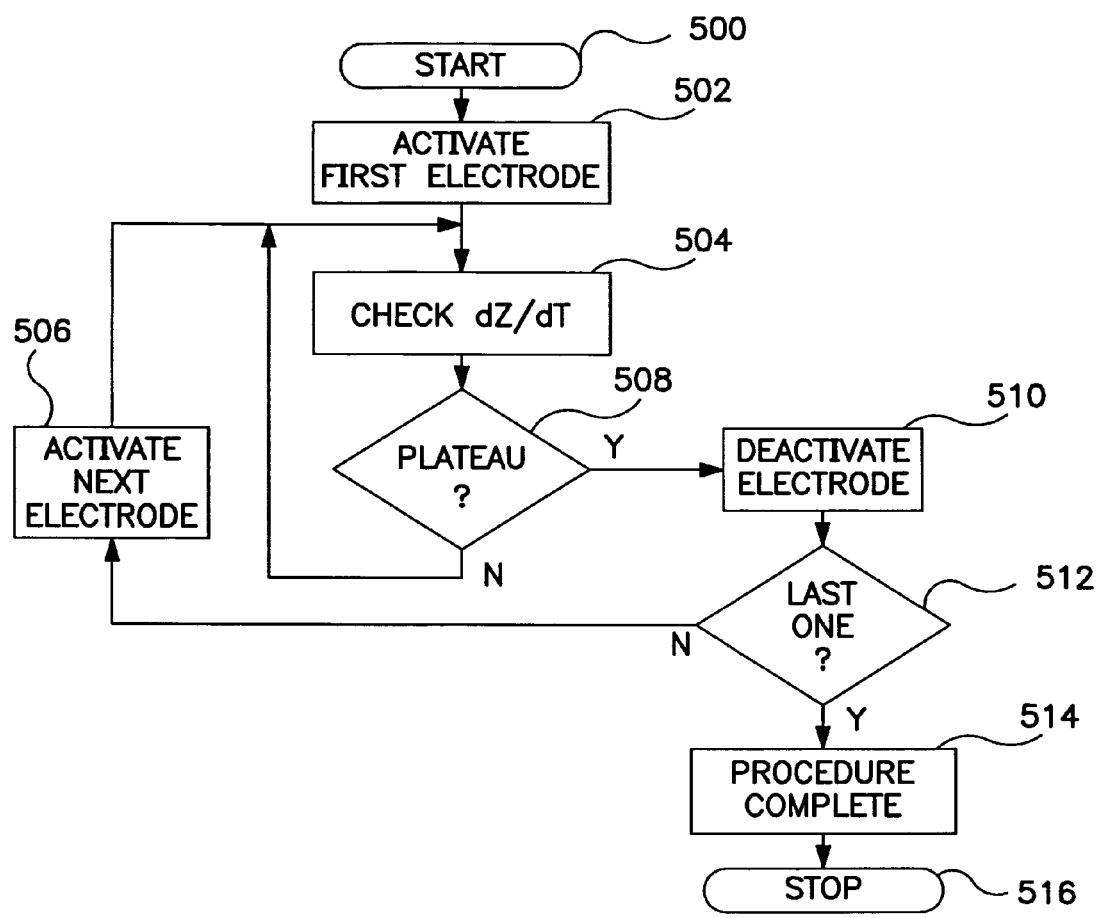
FIG. 8 illustrates a second mode of operation of a device as in FIG. 4 to activate and deactivate individual electrodes or electrode pairs.

FIG. 8 illustrates a functional flow chart of overall operation of a device in which a multi-electrode or multi-electrode pair ablation apparatus is employed, as in FIG. 7. In this embodiment, however, electrodes or electrode pairs are activated initially and sequentially. After initialization at 500, the microprocessor activates delivery of ablation energy to the first electrode at 502, checks dZ/dt and/or |dZ/dt| at 504 and, in the same manner as described for FIG. 7 above, checks to determine whether the impedance plateau criteria and/or other criteria as described above have been met. If so, the electrode is deactivated at 510. If not, application of ablation energy continues until the plateau criterion or other criteria are met as described above. After deactivation of an electrode at 510, the microprocessor checks to determine whether all electrodes have been activated and deactivated at 512, if not, the microprocessor then activates the next electrode at 506 and initiates delivery of ablation energy to that electrode. This process continues until the last electrode has been deactivated at 512, following which the microprocessor determines that the ablation process is complete at 514 and the ablation process is stopped at 516.

The overall operational methodology of FIG. 7 is believed to be desirable in that it allows for a more rapid completion of an ablation procedure. However, the overall operational method is described in FIG. 8 has the advantage that it may allow the use of a somewhat simplified generator because that multiple, separate impedance measurement circuits, power control circuits, and the like need not be provided for each electrode or electrode pair. A simple switching mechanism may be used in conjunction with only a single RF generator and impedance measurement circuit to successively apply energy to each electrode and to monitor impedance according to the invention.

FIGS. 9-12 show yet another aspect of the invention in which RF power delivery can also be controlled in order to assist in the assessment of lesion transmurality. The ablation commences at a first power level 600 and is then increased to a second power level 602 as certain conditions are satisfied. The power level can also be increased from the second power level to a third power level 604 and in the same stepwise manner, increasing the power level from an N power level to an n+1 power level until a set of conditions are met that indicates that transmurality has been achieved and/or that the power should be turned off. For example, an initial power level $P_0$ can be selected in the range of about 10 to 25 watts. The power level can then be rapidly increased to a second power level $P_1$ in an increment in the range of about 3 to 10 watts at a rate of at least about 0.5 watts/second. Subsequent power levels $P_2$, $P_3$, etc. can be similarly achieved. A maximum permitted power in the range of about 25-50 watts can also be selected to ensure that the power level is not raised beyond safe limits. Typical power levels could be an initial power level $P_0$ of about 25 watts and a second power level $P_1$ of about 30 watts. Power levels $P_2$, $P_3$, etc. could be increased in similar increments until a maximum power level of about 40 watts was achieved.

Figure 9:
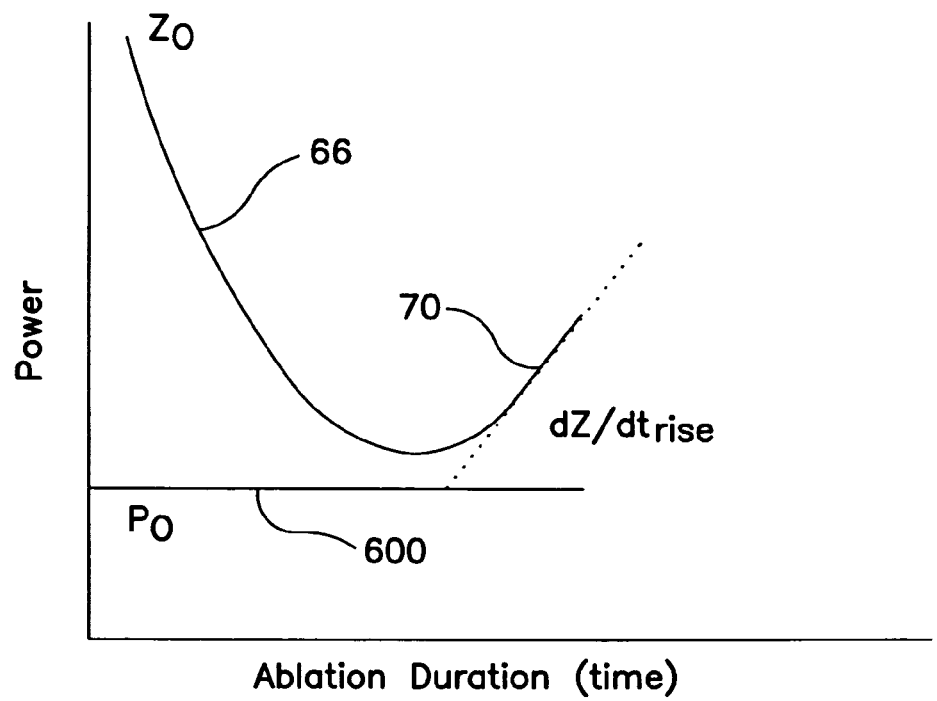
FIGS. 9-12 are graphs illustrating modes of operation for a device according to the present invention.
Figure 10:
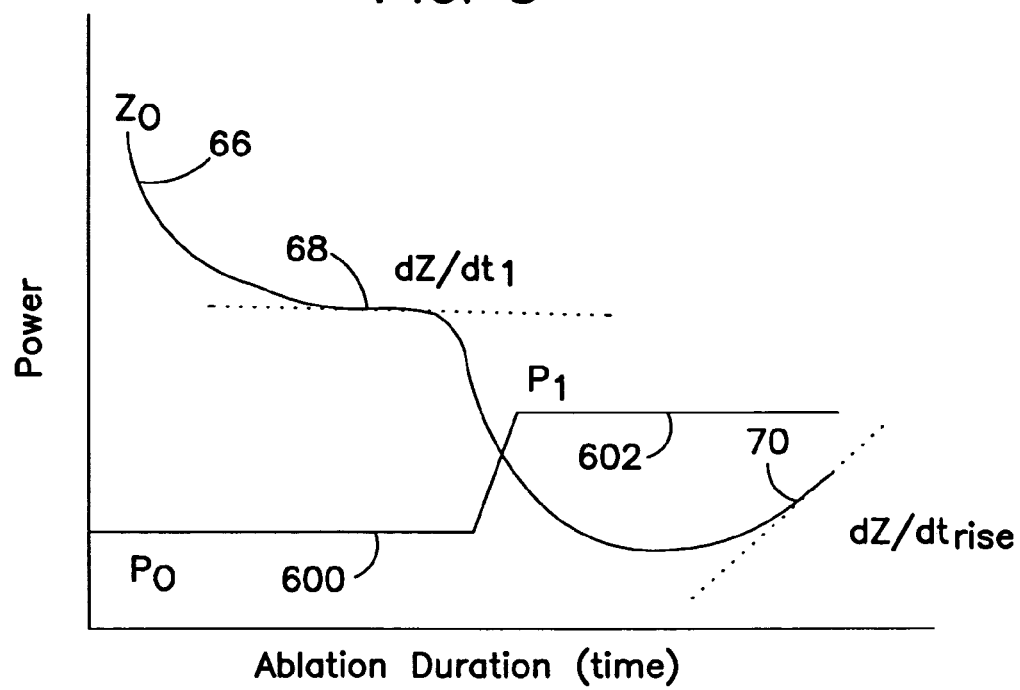
Figure 11:
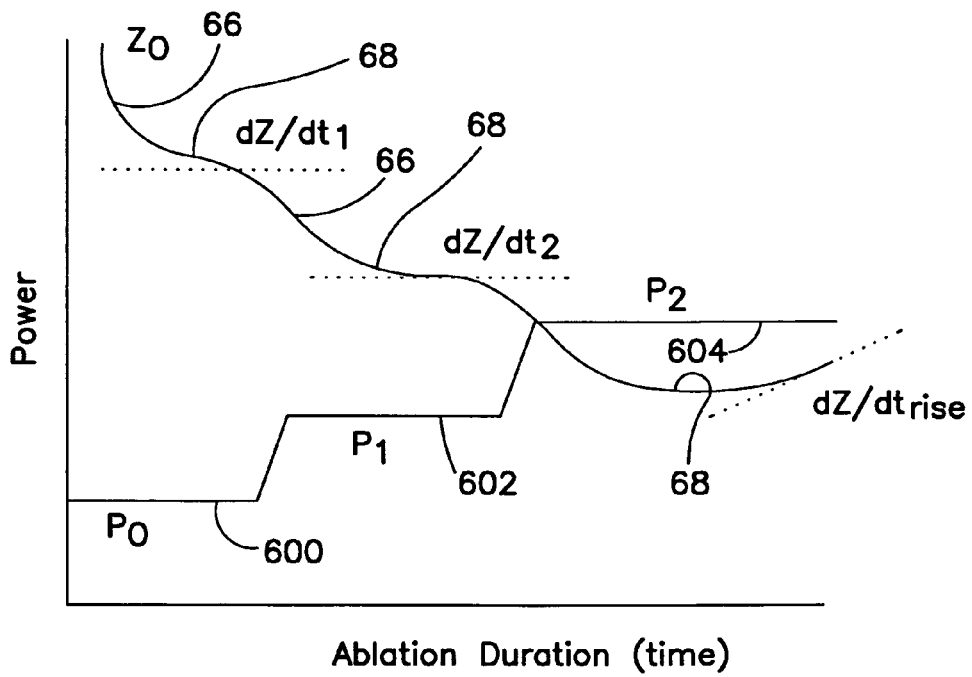
Figure 12:
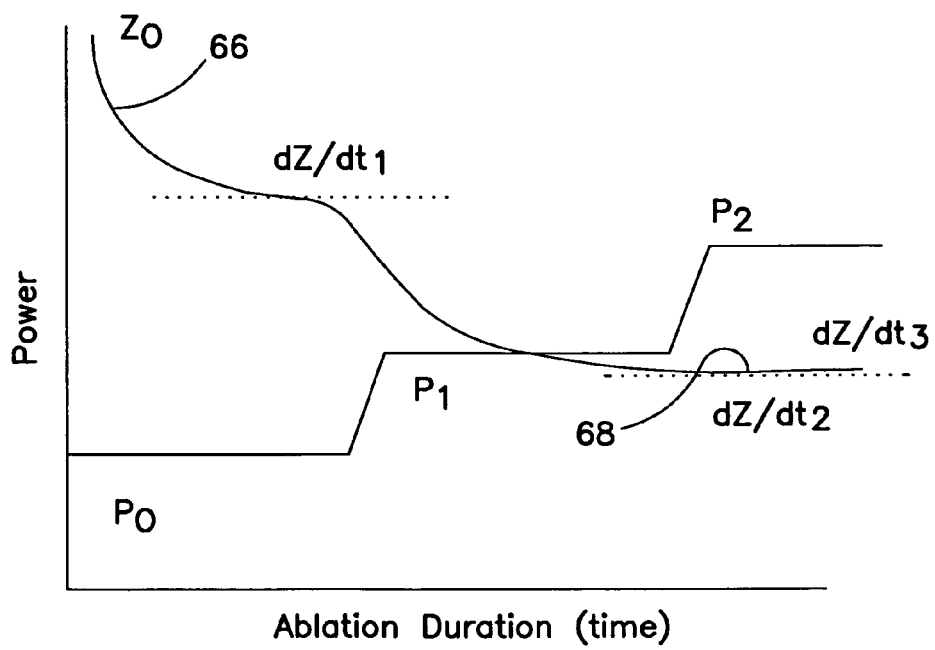

In each of the FIGS. 9-12, an initial selected power level $P_0$ is either maintained or increased to a second power level in response to changes in the detected impedance occurring during the ablation. In each case, the initial detected impedance $Z_0$ drops initially as ablation proceeds. However, each of FIGS. 9-12 shows exemplary alternative responses of a system according to the invention as differing impedance conditions are detected. In FIG. 9, the power level remains the same during the entire ablation procedure because a detected rapid rise in impedance $dZ/dt_{rise}$ is detected without first detecting a plateau. One condition indicating that transmurality has been achieved is a rapid rise in impedance 70 such as that shown in FIG. 9. Upon detecting a rapid rise in impedance 70, the power is turned off and the ablation for the lesion is completed. Conditions for an increase in power level can include one or more of: the detection of a plateau 68 in impedance or a slow rise in impedance or the achievement of a maximum permitted time for that power level. Conditions indicating that transmurality has been achieved can include one of: the lack of change in detected impedance in response to the change in power level or the detection of a rapid rise in impedance. FIG. 10 shows the detection of a plateau 68 in the impedance curve at $dZ/dt_1$, which triggers a rapid increase in power level from $P_0$ to $P_1$. The increase in power level causes a drop in impedance and therefore the ablation is continued at the second power level $P_1$ until the detected impedance indicates a rapid rise $dZ/dt_{rise}$. Upon detection of the rapid impedance rise, the power is turned off and the ablation for the lesion is completed. In the event that neither a plateau 68 or a rapid rise 70 is detected, ablation at the power level $P_0$ may be continued for a maximum pre-selected period of time followed by an increase in power level to power level $P_1$. For example, a time in the range of about 3 to 20 seconds, or more preferably about 8 seconds could be selected as the maximum duration for ablation at a particular power level. FIG. 11 shows the detection of a plateau 68 in impedance at $dZ/dt_1$ which triggers an increase in power level from $P_0$ to $P_1$. Because the impedance drops in response to the increased power level, ablation continues at the second power level $P_1$ until a second plateau 68 in impedance is detected at $dZ/dt_2$. The detection of the second impedance plateau triggers a second increase in power level, from $P_1$ to $P_2$. Because the impedance drops in response to the increase in power level, ablation is continued at the third power level $P_2$ until a rapid rise in impedance is detected at $dZ/dt_{rise}$. Upon detection of the rapid impedance rise, the power is turned off and the ablation for the lesion is completed. FIG. 12 shows the detection of a plateau in impedance at $dZ/dt_1$, which triggers an increase in power level from $P_0$ to $P_1$. Because the impedance drops in response to the increased power level, ablation continues at the second power level $P_1$ until a second plateau is detected at $dZ/dt_2$. The detection of the second plateau triggers a second increase in the power level from $P_1$ to $P_2$. Because the impedance does not drop in response to the increase in power level from $P_1$ to $P_2$, the continued plateau is verified by impedance measurement at $dZ/dt_3$ and the ablation is immediately terminated. Each of FIGS. 9-12 illustrates successful termination of ablation by detecting impedance that is characteristic of achievement of transmurality. If the detection of impedance does not indicate the achievement of transmurality, the ablation can still be terminated if the total time for the ablation exceeds a predetermined limit. For example, a total limit on ablation to form the lesion could take about 30 to 60 seconds, and preferably about 40 seconds. Alternatively, ablation could also be stopped upon reaching a maximum power level or after the completion of a predetermined number of power level increases.

Figure 13:
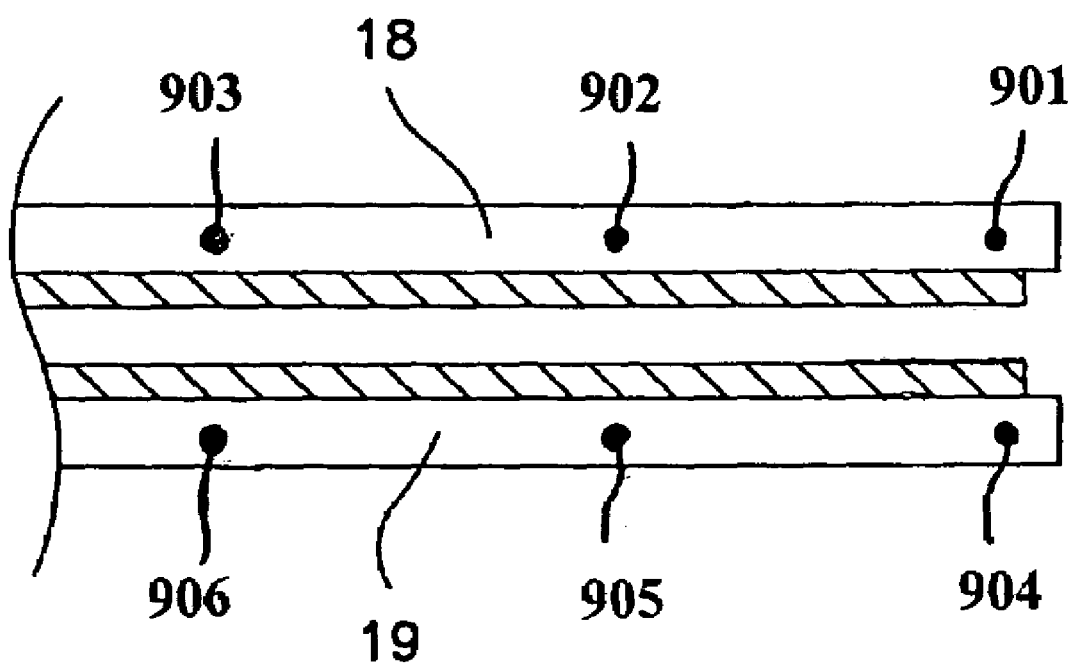
FIG. 13 illustrates an alternative configuration for a hemostat generally according to FIG. 1.

FIG. 13 shows yet another aspect of the invention in which complete or partial submersion of one or both of the jaws of the device in a fluid may be detected prior, during or following an ablation procedure. During the medical procedure, blood, cardiopulmonary bypass (CPB) fluids, such as cardioplegia fluids, and/or surgical field irrigation fluids can collect or pool in the atria and/or pericardial sac, for example. When the ablation device is positioned and/or clamped onto tissue, one or more electrodes of the device may become fully or partially submerged by one or more fluids. In addition, during the ablation procedure, the state of fluid contact with the electrodes may change. These changes in fluid contact with the electrodes may be caused by fluid levels changing or repositioning the tissue to be ablated. For example, the surgeon may reposition the heart or the ablation device during the ablation procedure, thereby changing the degree of submersion in fluid. In vitro and in vivo experiments have shown that total submersion, oscillating submersion, or partial submersion of one or more electrodes can cause impedance changes and affect the ablation cycle and lesion quality. For example, a low impedance shunt may be established between submerged electrodes. Impedance changes can make the implementation and reliability of a transmurality algorithm very challenging.

As shown in FIG. 13, submersion sensors 901, 902, 903, 904, 905, 906 may be incorporated into jaws 18 and 19 of ablation device 10, for example. Sensors 901, 902, 903, 904, 905, 906 can be used to determine if the electrodes are fully submerged, partially submerged, or are in a state of oscillation between submersion and non-submersion. Each sensor may be connected to an RF generator, for example to generator 799, by means of individually insulated conductors (not shown). The conductors can be routed through the ablation device similar to the RF conductors 21 and 22.

Through quantitative testing the optimum number and position or location of submersion sensors can be determined for individual ablation devices. For example, different ablation device designs may require a different number of sensors located at different positions.

One embodiment of the present invention includes an ablation system comprising a RF generator, for example generator 799, having a sensor interrogation program and an ablation device, for example as shown in FIG. 13, having submersion sensors. A signal can be sent from one sensor of a sensor pair and read at the other sensor of the sensor pair. For example, a signal may be sent from sensor 901 and the interrogation program determines if a signal is received at sensor 902. If a signal is received at sensor 902, sensors 901 and 902 would be determined to be submerged in fluid. The interrogation program then determines if a signal from sensor 901 is received at 903. If a signal is received at 903, then sensor 903 is also submerged in fluid. The interrogation program may continue to sample different sensor pairs to determine if the sensor pairs are submerged or not. Various signal vectors between the individual sensors may be randomly sampled throughout an ablation cycle. If no signal is detected between any sensor pair, the program would assume a non-submerged condition and the standard power and transmurality algorithm would be employed. If a signal is detected between any sensor pair, the program would interrogate the sensors and determine if the device is fully submerged, partially submerged or in an oscillating condition. Different power and transmurality algorithms, as discussed above, could be applied for the various degrees of submersion.

The signal transmitted from the submersion sensors needs to be physiologically compatible. It has been demonstrated that human and animal cells are affected or stimulated by frequencies below 10,000 Hz. For this reason, it is particularly important for cardiac ablation procedures on a beating heart to maintain frequencies above the 10,000 Hz, for example RF frequencies of about 100 KHz to about 100 MHz may be deployed. Signals transmitted from submersion sensors need to be discernable and/or isolated from the RF ablation current. Using different frequencies, modulation methods, or vector analysis of the signals can allow for simultaneous ablation and sensor monitoring. For example, a first reading of the sensor circuit could be accomplished when the ablation cycle is initiated. A built in delay in RF generator operation could allow for sampling of the sensor circuit prior to delivery of RF power to the ablation electrodes. Alternatively, pulsed RF may be used to perform the ablation procedure. Pulsed RF has been thought to provide benefits in creating ablation lesions. One benefit appears to be the avoidance of over ablating the surfaces closest to the ablation electrode. Pulsed RF has a pulse train of RF energy, wherein the RF energy is oscillated between being off and being on. During the off periods the sensor circuit could be sampled.

During an ablation process, submersion sensors may be in contact with various fluids and tissues having various differences in conductance, impedance, and capacitance. The sensor interrogation program would take into account these various differences. The sensor interrogation program may analyze the various vectors and resulting phase angle between the sensors. For example, it is known that current leads voltage in a capacitive circuit and lags voltage in a reactive circuit; ($P=E*I*Cos\ Q$; where P=power, E=voltage, I=amperage, and Cos Q=phase angle).

In one embodiment, the submersion sensors may be thermocouples thereby allowing for simultaneous temperature and submersion monitoring. Thermocouples generally would require filtering of RF noise. Thermocouples may sense a temperature gradient along the length of an ablation jaw. For example, a thermocouple in a fluid may be at a different temperature than a thermocouple in air or contacting tissue.

In one embodiment, the submersion sensors may be fiber optic sensors that would sample the light refraction between the various sensor locations. For example, air and water have different refraction indices, i.e., air=1.0003 vs. water=1.33. Depending on the light refraction each sensor senses or measures, it can be determined if the sensor is in air, fluid or placed against a tissue surface. Knowing the position of the sensors relative to the device determines what portion of the device is in air or a fluid, for example. A light refraction method has the advantage of being electrically isolated from the ablation current, thereby allowing simultaneous monitoring of submersion conditions while ablating tissue with RF energy. In one embodiment, the submersion sensors may employ ultrasound technology. As with the use of light refraction for monitoring changes in submersion, mechanical wave propagation in various materials could be monitored.

In one embodiment, segmented electrodes that are electrically isolated from each other may also serve as submersion sensors. For example, multiple electrodes of an ablation device, for example, as shown in FIG. 2b, could be used as submersion sensors as well as ablation elements. For example, electrode 56 on jaw 18 could transmit a signal that would be sensed or measured at electrode 58 on jaw 19. The sensor interrogation program could continue to evaluate all of the possible electrode combinations. The program could then determine if the portion of the device having the submersion sensors is fully submerged, partially submerged or in an oscillating condition. Different power and transmurality algorithms, as discussed above, could then be applied for the various degrees of submersion. The submersion sensors could also be used to determine if the jaws are fully clamped onto tissue or if they are only partially clamped onto tissue, i.e. a partial bite of tissue.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

We claim:

1. A method of ablating tissue, comprising:
    applying ablation energy from an ablation device along a surface of a first tissue site to create an electrically isolating lesion;
    monitoring a degree of submersion of at least a portion of the ablation device at the first tissue site; and
    responsive to the degree of submersion of the ablation device at the first tissue site, changing the application of ablating energy to the first tissue site.

2. The method of claim 1 wherein the applying of ablation energy to the first tissue site comprises applying RF energy.

3. The method of claim 1 wherein the step of monitoring the degree of submersion of at least a portion of the ablation device at the first tissue site comprises monitoring submersion using one or more submersion sensors.

4. The method of claim 3 wherein the submersion sensors comprise an electrode.

5. The method of claim 3 wherein the submersion sensors comprise a fiber optic sensor.

6. The method of claim 3 wherein the submersion sensors comprise a thermocouple.

7. The method of claim 1 wherein the applying of ablation energy to the first tissue site comprises applying RF energy using an irrigated RF electrode.

8. The method of claim 1 wherein the application of ablating energy to the first tissue site is increased in response to the degree of submersion of the ablation device at the first tissue site.

9. The method of claim 1 wherein the application of ablating energy to the first tissue site is decreased in response to the degree of submersion of the ablation device at the first tissue site.

10. The method of claim 1, further comprising:
    applying ablation energy from the ablation device along a surface of a second tissue site to create an electrically isolating lesion;
    monitoring the degree of submersion of at least a portion of the ablation device at the second tissue site; and
    responsive to the degree of submersion of the ablation device at the second tissue site, changing the application of ablating energy to the second tissue site.

11. The method of claim 10 wherein the applying of ablation energy to the second tissue site comprises applying RF energy.

12. The method of claim 10 wherein the step of monitoring the degree of submersion of at least a portion of the ablation device at the second tissue site comprises monitoring submersion using one or more submersion sensors.

13. The method of claim 12 wherein the submersion sensors comprise an electrode.

14. The method of claim 12 wherein the submersion sensors comprise a fiber optic sensor.

15. The method of claim 12 wherein the submersion sensors comprise a thermocouple.

16. The method of claim 10 wherein the applying of ablation energy to the second tissue site comprises applying RF energy using an irrigated RF electrode.

17. The method of claim 10 wherein the application of ablating energy to the second tissue site is increased in response to the degree of submersion of the ablation device at the second tissue site.

18. The method of claim 10 wherein the application of ablating energy to the second tissue site is decreased in response to the degree of submersion of the ablation device at the second tissue site.

* * * * *